(12) United States Patent
Michihata

(10) Patent No.: US 12,089,802 B2
(45) Date of Patent: Sep. 17, 2024

(54) MEDICAL IMAGE PROCESSING APPARATUS AND MEDICAL OBSERVATION SYSTEM

(71) Applicant: Sony Olympus Medical Solutions Inc., Tokyo (JP)

(72) Inventor: Taihei Michihata, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 12 days.

(21) Appl. No.: 17/182,268

(22) Filed: Feb. 23, 2021

(65) Prior Publication Data
US 2021/0290037 A1    Sep. 23, 2021

(30) Foreign Application Priority Data

Mar. 17, 2020  (JP) ................................ 2020-047012
Dec. 25, 2020  (JP) ................................ 2020-216975

(51) Int. Cl.
*A61B 1/00*  (2006.01)
*A61B 1/04*  (2006.01)
*A61B 1/06*  (2006.01)

(52) U.S. Cl.
CPC ...... *A61B 1/00009* (2013.01); *A61B 1/00188* (2013.01); *A61B 1/043* (2013.01); *A61B 1/0638* (2013.01); *A61B 1/0655* (2022.02); *A61B 1/0661* (2013.01)

(58) Field of Classification Search
CPC .............................................. A61B 1/00006
See application file for complete search history.

(56) References Cited

U.S. PATENT DOCUMENTS

2007/0055104 A1*  3/2007  Kumei ..................... A61B 1/04
                                                          600/176
2007/0260214 A1*  11/2007 Mikkaichi .......... A61B 1/00181
                                                          604/500
2010/0245550 A1*  9/2010  Ishihara ................. A61B 1/043
                                                          348/E7.085

(Continued)

FOREIGN PATENT DOCUMENTS

JP    2008259722 A    10/2008
JP    2012016545 A    1/2012

(Continued)

*Primary Examiner* — John P Leubecker
*Assistant Examiner* — Jae Woo
(74) *Attorney, Agent, or Firm* — XSENSUS LLP

(57) ABSTRACT

A medical image processing apparatus includes: a captured image acquisition unit configured to acquire a first captured image obtained by capturing light from an observation target to which light of a first wavelength band is emitted and a second captured image obtained by capturing fluorescence from the observation target excited by excitation light of a second wavelength band; an evaluation value calculation unit configured to calculate, based on the first captured image, an evaluation value used for at least one of a first control of controlling a focus position of an imaging device configured to generate each of the first captured image and the second captured image and a second control of controlling a brightness of the first captured image and the second captured image; and an operation controller configured to execute at least one of the first control and the second control based on the evaluation value.

28 Claims, 12 Drawing Sheets

(56) References Cited

U.S. PATENT DOCUMENTS

| | | | |
|---|---|---|---|
| 2015/0173595 A1* | 6/2015 | Takekoshi | A61B 1/045 600/317 |
| 2018/0242827 A1* | 8/2018 | Michihata | H04N 5/35554 |
| 2018/0242830 A1* | 8/2018 | Michihata | A61B 1/00188 |
| 2018/0243043 A1* | 8/2018 | Michihata | A61B 1/000095 |
| 2020/0008650 A1* | 1/2020 | Michihata | A61B 1/0661 |
| 2020/0029010 A1* | 1/2020 | Michihata | G02B 23/26 |
| 2021/0281731 A1* | 9/2021 | Michihata | H04N 5/232123 |
| 2021/0290035 A1* | 9/2021 | Michihata | A61B 1/0655 |
| 2021/0290036 A1* | 9/2021 | Segawa | A61B 1/0655 |
| 2021/0290037 A1* | 9/2021 | Michihata | A61B 1/00009 |
| 2021/0297575 A1* | 9/2021 | Michihata | H04N 5/2256 |
| 2021/0338040 A1* | 11/2021 | Michihata | A61B 1/045 |

FOREIGN PATENT DOCUMENTS

| | | | | |
|---|---|---|---|---|
| JP | 2012090726 A | 5/2012 | | |
| JP | 2016-202726 A | 12/2016 | | |
| WO | WO-2012090726 A1 | 7/2012 | | |
| WO | WO-2015012096 A1 * | 1/2015 | | A61B 1/00006 |
| WO | WO-2015015839 A1 | 2/2015 | | |
| WO | WO-2019087557 A1 | 5/2019 | | |

* cited by examiner

MEDICAL IMAGE PROCESSING APPARATUS AND MEDICAL OBSERVATION SYSTEM

CROSS-REFERENCE TO RELATED APPLICATIONS

This application claims priority from Japanese Application No. 2020-047012, filed on Mar. 17, 2020 and Japanese Application No. 2020-216975, filed on Dec. 25, 2020, the contents of each are incorporated by reference herein in its entirety.

BACKGROUND

The present disclosure relates to a medical image processing apparatus and a medical observation system.

In the related art, there is a known photodynamic diagnosis apparatus for performing photodynamic diagnosis (PDD), which is one of cancer diagnosis methods for detecting cancer cells (refer to, for example, JP 2016-202726 A).

In photodynamic diagnosis, for example, a photosensitive substance such as 5-aminolevulinic acid (hereinafter referred to as 5-ALA) is used. The 5-ALA is a natural amino acid originally contained in the living body of animals and plants. This 5-ALA is taken up into cells after administration into the body and biosynthesized into protoporphyrin in mitochondria. Cancer cells accumulate the protoporphyrin excessively. In addition, protoporphyrin that is excessively accumulated in the cancer cells is photoactive. Therefore, when excited with excitation light (for example, blue visible light in the wavelength band of 375 nm to 445 nm), the protoporphyrin emits fluorescence (red fluorescence in the wavelength band of 600 nm to 740 nm, for example). A cancer diagnosis method in which a light-sensitive substance is used to fluoresce cancer cells in this manner is referred to as photodynamic diagnosis.

The photodynamic diagnosis apparatus described in JP 2016-202726 A includes: a fluorescence imaging device that captures fluorescence from a photosensitive substance excited by excitation light to generate a fluorescence image; and an optical filter provided in an optical path front stage of the fluorescence imaging device and configured to cut off entire excitation light directed toward the fluorescence imaging device.

SUMMARY

Meanwhile, signal levels are remarkably low in a fluorescence image because the fluorescence from the light-sensitive substance is minute.

Therefore, in calculating the evaluation value used for a first control of controlling a focus position of an imaging unit and a second control of controlling the brightness of the fluorescence image based on the fluorescence image, it would be difficult to calculate an appropriate evaluation value.

Here, it is conceivable to include an excitation light component into the fluorescence image by partially transmitting the excitation light without cutting off the entire excitation light directed to the fluorescence imaging device by the optical filter. Unfortunately, however, excitation light is not light in the green wavelength band that contributes to the brightness having high visibility to human eyes, but the light in the blue wavelength band that has less contribution to the brightness. Therefore, even when the above-described evaluation value is calculated based on the fluorescence image containing the excitation light component, it would be still difficult to calculate an appropriate evaluation value similarly to the above.

Due to the above, there is a problem that inappropriately calculated evaluation values lead to difficulty in appropriate execution of the first control and the second control, and a failure in generation of an image suitable for observation.

According to one aspect of the present disclosure, there is provided a medical image processing apparatus including: a captured image acquisition unit configured to acquire a first captured image obtained by capturing light from an observation target to which light of a first wavelength band is emitted and a second captured image obtained by capturing fluorescence from the observation target excited by excitation light of a second wavelength band different from the first wavelength band; an evaluation value calculation unit configured to calculate, based on the first captured image, an evaluation value to be used for at least one of a first control of controlling a focus position of an imaging device configured to generate each of the first captured image and the second captured image and a second control of controlling a brightness of the first captured image and the second captured image; and an operation controller configured to execute at least one of the first control and the second control based on the evaluation value.

DETAILED DESCRIPTION

Figure 1:
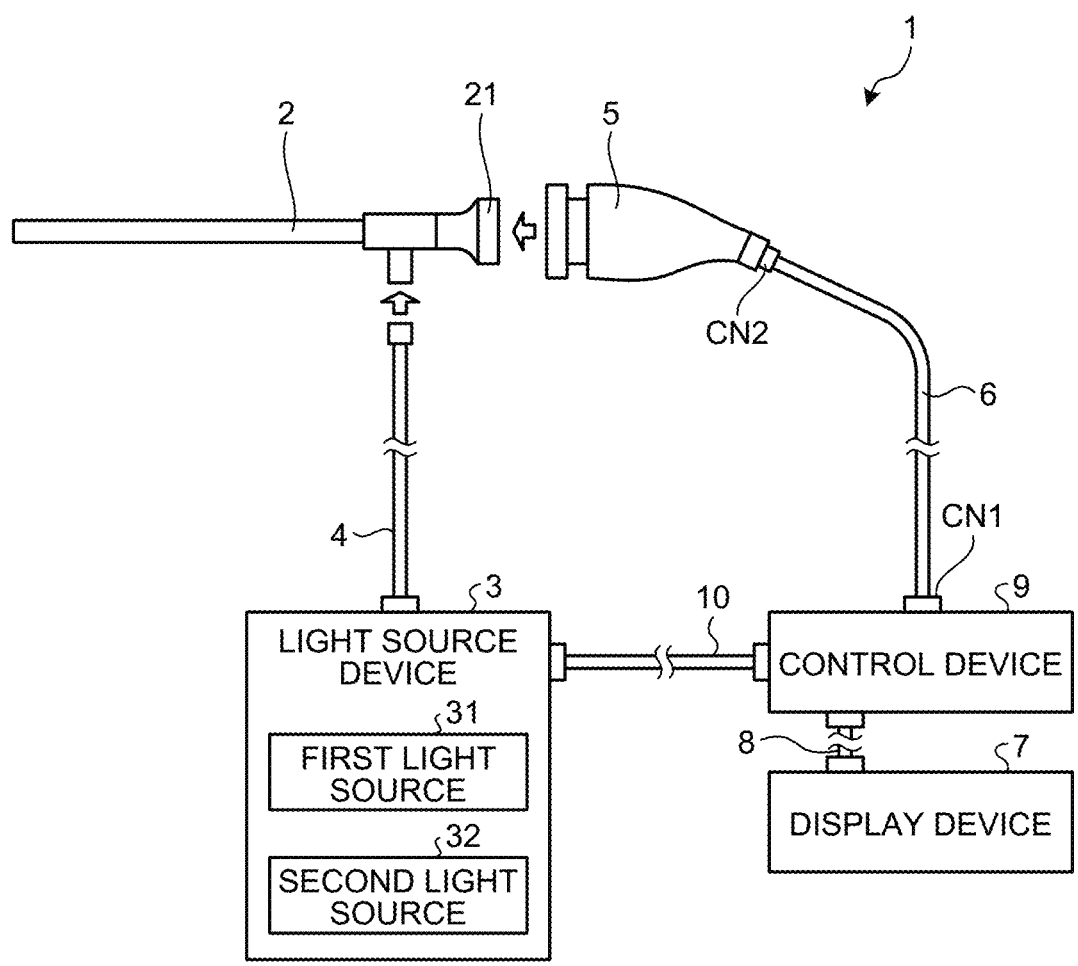
FIG. 1 is a view illustrating a configuration of a medical observation system according to a first embodiment.

Hereinafter, modes for carrying out the present disclosure (hereinafter referred to as embodiments) will be described with reference to the drawings. Note that the present disclosure is not limited to the embodiments described below. In the drawings, same reference signs are attached to the same components.

First Embodiment

Schematic configuration of medical observation system FIG. 1 is a view illustrating a configuration of a medical observation system 1 according to a first embodiment.

The medical observation system 1 is a system used in the medical field to capture (observe) inside the living body (observation target) as a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 is implemented by a rigid endoscope. That is, the insertion unit 2 has an elongated shape that is entirely rigid, or partially rigid with a partially flexible portion, so as to be inserted into a living body. The insertion unit 2 includes an optical system having one or more lenses and configured to collect light from inside of the living body.

The light source device 3 is connected to one end of the light guide 4, and supplies light to be applied to the inside of the living body to the one end of the light guide 4 under the control of the control device 9. As illustrated in FIG. 1, the light source device 3 includes a first light source 31 and a second light source 32.

The first light source 31 emits light (performs light emission) in the first wavelength band. In the first embodiment, the first light source 31 emits white light. Examples of the first light source 31 include a light emitting diode (LED), a semiconductor laser, or the like.

The second light source 32 emits excitation light (performs light emission) in a second wavelength band different from the first wavelength band. In the first embodiment, the second light source 32 emits excitation light in the blue wavelength band (for example, the wavelength band of 375 nm to 445 nm) that excites protoporphyrin. Examples of the second light source 32 include an LED, a semiconductor laser, or the like. Furthermore, when excited by the excitation light, protoporphyrin emits fluorescence in a red wavelength band (for example, a wavelength band of 600 nm to 740 nm). In the light source device 3, the first light source 31 is driven in a first period out of the first and second periods that are alternately repeated under the control of the control device 9. That is, the light source device 3 emits white light (hereinafter referred to as normal light) in the first period. Furthermore, in the light source device 3, the second light source 32 is driven in the second period under the control of the control device 9. That is, the light source device 3 emits excitation light in the second period.

Note that the first light source 31 may be a light source that includes an LED that emits light in the red wavelength band, an LED that emits light in the green wavelength band, and an LED that emits light in the blue wavelength band and that is configured to emit white light by controlling the three LEDs to emit light at the same time. Furthermore, the second light source 32 may be an LED that emits light in the blue wavelength band among the three LEDs.

In the first embodiment, the light source device 3 is separated from the control device 9. However, the configuration is not limited to this, and it is allowable to employ a configuration in which the light source device 3 is provided inside the control device 9.

The light guide 4 has one end detachably connected to the light source device 3 and the other end detachably connected to the insertion unit 2. The light guide 4 transmits the light (normal light and excitation light) supplied from the light source device 3 from one end to the other end and supplies the light to the insertion unit 2. The light supplied to the insertion unit 2 is emitted from a distal end of the insertion unit 2 and directed into the living body. When normal light (white light) is emitted into the living body, the normal light reflected in the living body is collected by an optical system in the insertion unit 2. In the following, for convenience of explanation, the normal light collected by the optical system in the insertion unit 2 will be referred to as a first subject image. When the excitation light is emitted into the living body, the excitation light reflected in the living body, and fluorescence emitted from the protoporphyrin, which occurs when the protoporphyrin accumulated in a lesion in the living body is excited by the excitation light, are collected by the optical system in the insertion unit 2. In the following, for convenience of explanation, the excitation light and fluorescence collected by the optical system in the insertion unit 2 will be referred to as a second subject image.

The camera head 5 corresponds to an imaging device according to the present disclosure. The camera head 5 is detachably connected to a proximal end (an eyepiece 21 (FIG. 1)) of the insertion unit 2. Under the control of the control device 9, the camera head 5 captures the first subject image (normal light) and the second subject image (excitation light and fluorescence) collected by the insertion unit 2, and outputs an image signal (RAW signal) obtained by the capturing. The image signal is an image signal of 4K resolution or more.

A detailed configuration of the camera head 5 will be described below.

The first transmission cable 6 has one end detachably connected to the control device 9 via a connector CN1 (FIG. 1), and has the other end detachably connected to the camera head 5 via a connector CN2 (FIG. 1). The first transmission cable 6 transmits the image signal or the like output from the camera head 5 to the control device 9, and transmits a control signal, a synchronization signal, a clock, power, or the like output from the control device 9 to the camera head 5 individually.

Note that the image signal or the like transmitted from the camera head 5 to the control device 9 via the first transmission cable 6 may be transmitted in an optical signal or in an electrical signal. The similar applies to transmission of the control signal, the synchronization signal, and the clock from the control device 9 to the camera head 5 via the first transmission cable 6.

The display device 7 is implemented by a display using liquid crystal, organic Electro Luminescence (EL), or the like, and displays an image based on a video signal from the control device 9 under the control of the control device 9.

The second transmission cable 8 has one end detachably connected to the display device 7 and the other end detachably connected to the control device 9. The second transmission cable 8 transmits the video signal processed by the control device 9 to the display device 7.

The control device 9 corresponds to the medical image processing apparatus according to the present disclosure. The control device 9 is implemented by a central processing unit (CPU), a field-programmable gate array (FPGA), or the like, and comprehensively controls operation of the light source device 3, the camera head 5, and the display device 7.

The detailed configuration of the control device 9 will be described below.

The third transmission cable 10 has one end detachably connected to the light source device 3 and the other end detachably connected to the control device 9. The third transmission cable 10 transmits the control signal from the control device 9 to the light source device 3.

Configuration of Camera Head

Next, a configuration of the camera head 5 will be described.

Figure 2:
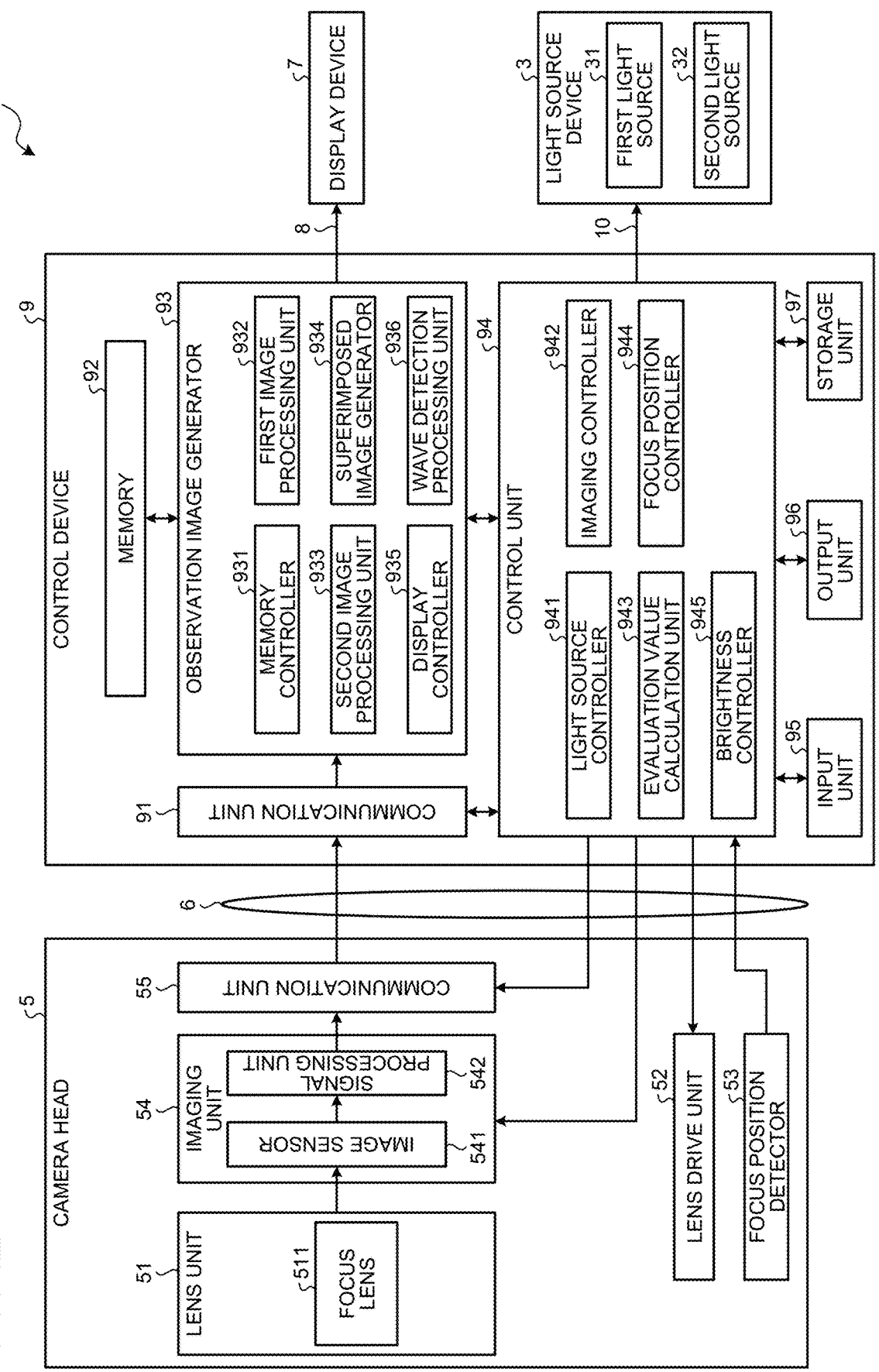
FIG. 2 is a block diagram illustrating a configuration of a camera head and a control device.

FIG. 2 is a block diagram illustrating a configuration of the camera head 5 and the control device 9.

For convenience of explanation, FIG. 2 omits illustration of connectors CN1 and CN2 between the control device 9 and the first transmission cable 6 and between the camera head 5 and the first transmission cable 6, and connectors between the control device 9 and the second transmission cable 8 and between the display device 7 and the second transmission cable 8, and connectors between the control device 9 and the third transmission cable 10 and between the light source device 3 and the third transmission cable 10.

As illustrated in FIG. 2, the camera head 5 includes a lens unit 51, a lens drive unit 52, a focus position detector 53, an imaging unit 54, and a communication unit 55.

The lens unit 51 includes a focus lens 511, and forms a first subject image (normal light) and a second subject image (excitation light and fluorescence) focused by the insertion unit 2 onto an imaging surface of the imaging unit 54 (image sensor 541).

The focus lens 511 is constituted with one or more lenses and adjusts the focus position by moving along an optical axis.

Furthermore, the lens unit 51 includes a focus mechanism (not illustrated) for moving the focus lens 511 along the optical axis.

Under the control of the control device 9, the lens drive unit 52 operates the above-described focus mechanism in an AF process described below executed by the control device 9 and adjusts the focus position of the lens unit 51.

The focus position detector 53 is constituted with a position sensor such as a photo-interrupter, and detects the current position (focus position) of the focus lens 511. Subsequently, the focus position detector 53 outputs a signal corresponding to the detected focus position to the control device 9.

The imaging unit 54 captures the inside of the living body under the control of the control device 9. As illustrated in FIG. 2, the imaging unit 54 includes the image sensor 541 and a signal processing unit 542.

The image sensor 541 is constituted with a charge coupled device (CCD), complementary metal oxide semiconductor (CMOS) or the like that receives the first subject image (normal light) and the second subject image (excitation light and fluorescence) formed by the lens unit 51 and converts the image into electrical signals (analog signals). Under the control of the control device 9, the image sensor 541 performs capturing in synchronization with the light emission timing of the light source device 3, in each of first and second periods that are alternately repeated. In the following, for convenience of explanation, the image generated by capturing the first subject image (normal light) with the image sensor 541 in the first period will be referred to as a normal light image (corresponding to a first captured image according to the present disclosure), and the image generated by capturing the second subject image (excitation light and fluorescence) with the image sensor 541 in the second period will be referred to as a PDD image (corresponding to a second captured image according to the present disclosure). In addition, the normal light image and the PDD image will be collectively referred to as a captured image.

Under the control of the control device 9, the signal processing unit 542 performs signal processing on the captured image (analog signal) generated by the image sensor 541 and outputs the captured image (RAW signal (digital signal)).

For example, the signal processing unit 542 performs signal processing such as processing of removing reset noise, processing of multiplying an analog gain to amplify the analog signal, A/D conversion, or the like on the captured image (analog signal) generated on the image sensor 541.

The communication unit 55 functions as a transmitter that transmits the captured image (RAW signal (digital signal)) output from the imaging unit 54 to the control device 9 via the first transmission cable 6. For example, the communication unit 55 includes a high-speed serial interface that performs captured image communication with the control device 9 via the first transmission cable 6 at a transmission rate of 1 Gbps or more.

Configuration of Control Device

Next, the configuration of the control device 9 will be described with reference to FIG. 2.

As illustrated in FIG. 2, the control device 9 includes a communication unit 91, memory 92, an observation image generator 93, a control unit 94, an input unit 95, an output unit 96, and a storage unit 97.

The communication unit 91 functions as a receiver that receives the captured image (RAW signal (digital signal)) output from the camera head 5 (communication unit 55) via the first transmission cable 6. That is, the communication unit 91 corresponds to a captured image acquisition unit according to the present disclosure. For example, the communication unit 91 includes a high-speed serial interface that performs captured image communication with the communication unit 55 at a transmission rate of 1 Gbps or more.

The memory 92 is constituted with dynamic random access memory (DRAM) or the like. The memory 92 may temporarily store a plurality of frames of captured images sequentially output from the camera head 5 (communication unit 55).

Under the control of the control unit 94, the observation image generator 93 processes the captured image (RAW signal (digital signal)) sequentially output from the camera head 5 (communication unit 55) and received by the communication unit 91. As illustrated in FIG. 2, the observation image generator 93 includes a memory controller 931, a first image processing unit 932, a second image processing unit 933, a superimposed image generator 934, a display controller 935, and a wave detection processing unit 936.

The memory controller 931 controls writing and reading of the captured image to and from the memory 92. More specifically, the memory controller 931 sequentially writes the captured images (normal light image and PDD image) that are sequentially output from the camera head 5 (communication unit 55) and received by the communication unit 91, to the memory 92. Furthermore, the memory controller 931 reads a normal light image from the memory 92 at a specific timing, and controls the first image processing unit 932 to input the read normal light image. Furthermore, the memory controller 931 reads a PDD image from the memory 92 at a specific timing, and controls the second image processing unit 933 to input the read PDD image.

The first image processing unit 932 executes first image processing on the input normal light image (RAW signal (digital signal)).

Examples of the first image processing includes optical black subtraction processing, a white balance adjustment process, digital gain processing, demosaic processing, color correction matrix processing, gamma correction processing, YC processing of converting RGB signals (normal light image) into a luminance signal and color difference signals (Y, CB/CR signals), or the like.

The second image processing unit 933 executes second image processing different from the first image processing on the input PDD image (RAW signal (digital signal)).

Similarly to the first image processing as above, examples of the second image processing includes optical black subtraction processing, a white balance adjustment process, digital gain processing, demosaic processing, color correction matrix processing, a gamma correction processing, YC processing of converting RGB signals (PDD images) into a luminance signal and color difference signals (Y, CB/CR signals), or the like.

In addition, the second image processing includes an adjustment process and a color change process illustrated below.

The adjustment process is a process of deleting components (including the excitation light component) other than the fluorescence component, contained in the PDD image. Specifically, the excitation light is light in the blue wavelength band. Fluorescence is light in the red wavelength band. Therefore, in the adjustment process, among the R, G, and B pixel values included in the PDD image, the components (G value and excitation light component (B value)) other than the fluorescence component (R value) are deleted. (G and B values are set to "0").

For example, in the white balance adjustment process, by appropriately adjusting the gain to be multiplied by each of pixel values of R, G, and B, it is possible to delete G and B values other than the R value among the pixel values of R, G, and B included in the PDD image. Furthermore, for example, when R value, G value, and B value are given to each of pixels by interpolation in demosaic processing, it is possible to delete G and B values other than R value among R, G, and B pixel values included in the PDD image. Furthermore, for example, in the color correction matrix processing, by appropriately adjusting the color correction matrix to be multiplied with the input matrix having each of pixel values of R, G, B included in the PDD image as a matrix element, it is possible to delete the G and B values other than R value among the R, G, and B pixel values included in the PDD image.

The color change process is a process performed in an entire image area of a PDD image, in which the pixel position where the luminance value is a specific threshold or more (pixel position where protoporphyrin is excited) is changed to a specific color (for example, a color different from fluorescence (red)).

The superimposed image generator 934 executes a superimposition process in which a PDD image that has undergone the second image processing executed by the second image processing unit 933 is superimposed over the normal light image that has undergone the first image processing executed by the first image processing unit 932 so as to generate a superimposed image.

Here, the superimposition process includes a first superimposition process and a second superimposition process illustrated below, as an example. In the PDD image, an area formed with pixels having a luminance value of a specific threshold or more will be referred to as a fluorescence area.

The first superimposition process is a process of replacing an area having the same pixel position as the fluorescence area in a normal light image with an image of the fluorescence area in the PDD image.

The second superimposition process is a process of changing the brightness of the color indicating fluorescence given to each of pixels in the area having the same pixel position as the fluorescence area in the normal light image in accordance with the luminance value of each of the pixel positions in the fluorescence area of the PDD image.

Under the control of the control unit 94, the display controller 935 generates a video signal for displaying the superimposed image generated by the superimposed image generator 934. Subsequently, the display controller 935 outputs the video signal to the display device 7 via the second transmission cable 8.

The wave detection processing unit 936 executes a wave detection process based on the normal light image that has undergone the first image processing executed by the first image processing unit 932.

For example, based on pixel information (for example, a luminance signal (Y signal)) for each of pixels in a wave detection area which is at least a partial area of the entire image area of one-frame normal light image, the wave detection processing unit 936 executes detection of the contrast and frequency components of the image within the wave detection area, detection of the luminance mean value and the maximum/minimum luminance pixels in the wave detection area using a filter or the like, determination by comparison with a threshold, and detection of the histogram or the like (wave detection process). Subsequently, the wave detection processing unit 936 outputs the wave detection information (contrast, frequency component, a luminance mean value, maximum/minimum luminance pixels, histogram, or the like) obtained by the wave detection process to the control unit 94.

The control unit 94 is constituted by using a CPU, FPGA, or the like, for example, and outputs a control signal via the first to third transmission cables 6, 8 and 10, thereby controlling operations of the light source device 3, the camera head 5, and the display device 7, as well as controlling entire operation of the control device 9. As illustrated in FIG. 2, the control unit 94 includes a light source controller 941, an imaging controller 942, an evaluation value calculation unit 943, a focus position controller 944, and a brightness controller 945. The functions of the light source controller 941, the imaging controller 942, the evaluation value calculation unit 943, the focus position controller 944, and the brightness controller 945 will be described in "Operation of control device" described below.

The input unit 95 is constituted with an operation device such as a mouse, a keyboard, and a touch panel, and receives user operations performed by a user such as a doctor. Subsequently, the input unit 95 outputs an operation signal corresponding to the user operation to the control unit 94.

The output unit 96 is constituted with a speaker, a printer, or the like, and outputs various types of information.

The storage unit 97 stores a program executed by the control unit 94, information needed for processing performed by the control unit 94, or the like.

Operation of Control Device

Next, operation of the above-described control device 9 will be described.

Figure 3:
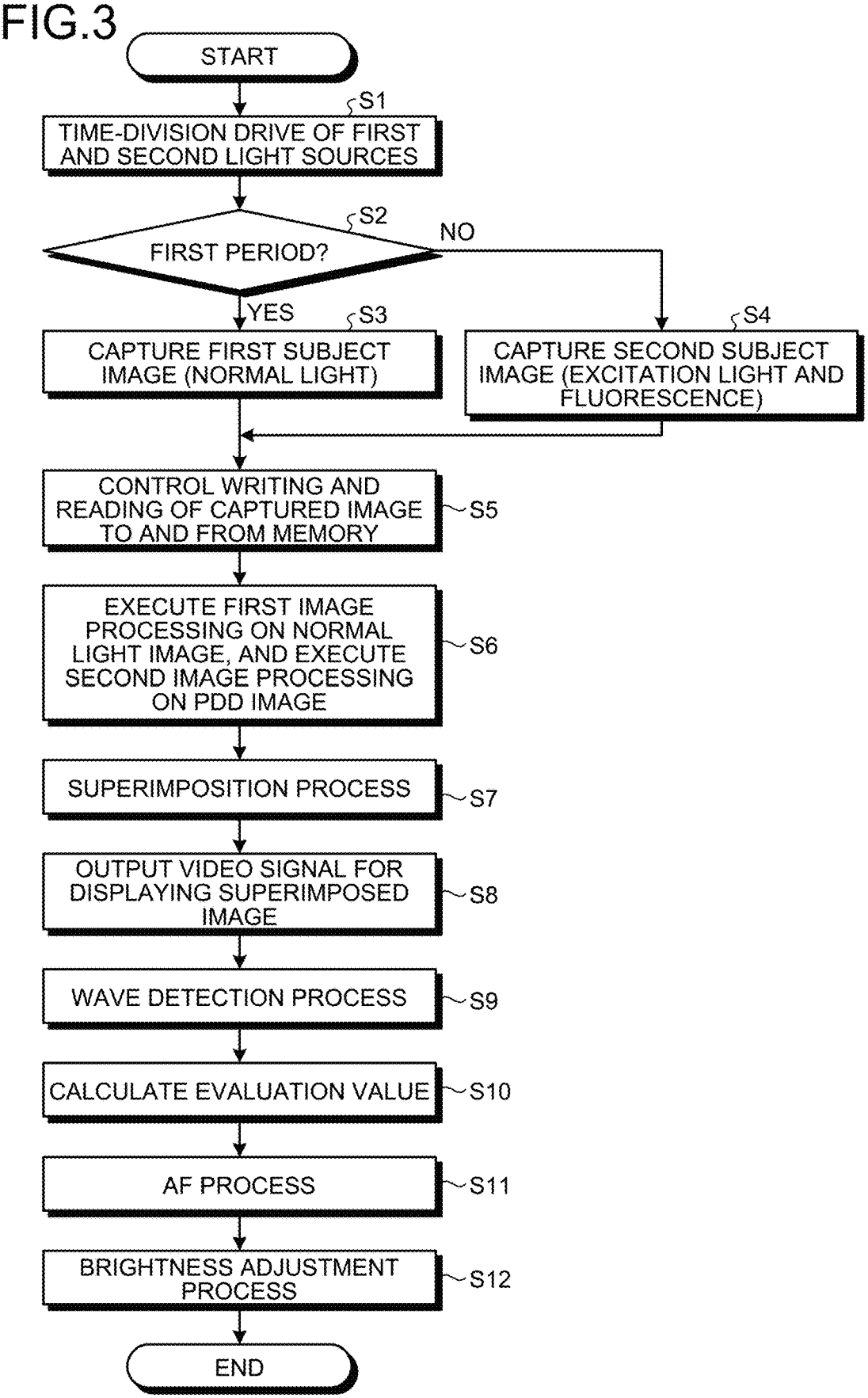
FIG. 3 is a flowchart illustrating operation of a control device.
Figure 4:
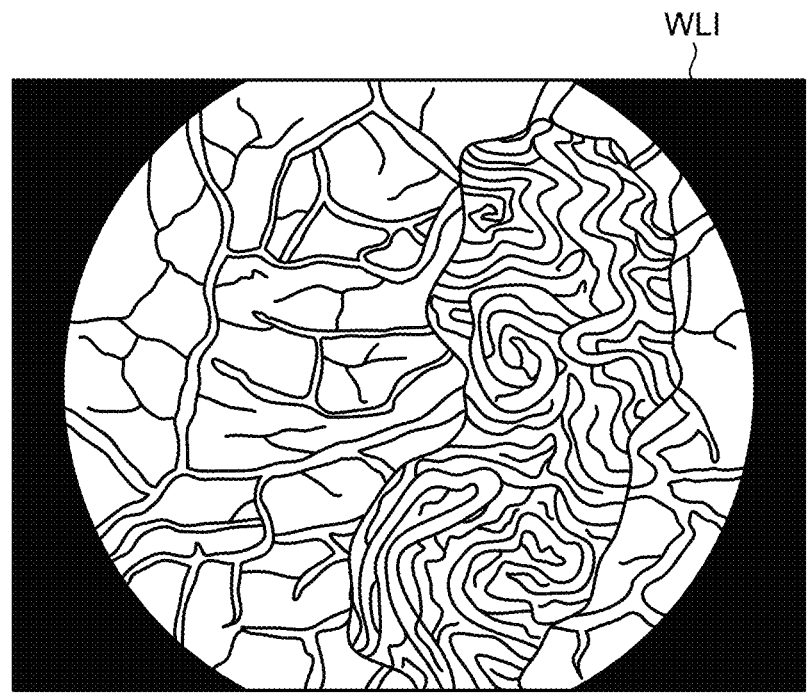
FIG. 4 is a diagram illustrating operation of a control device.
Figure 5:
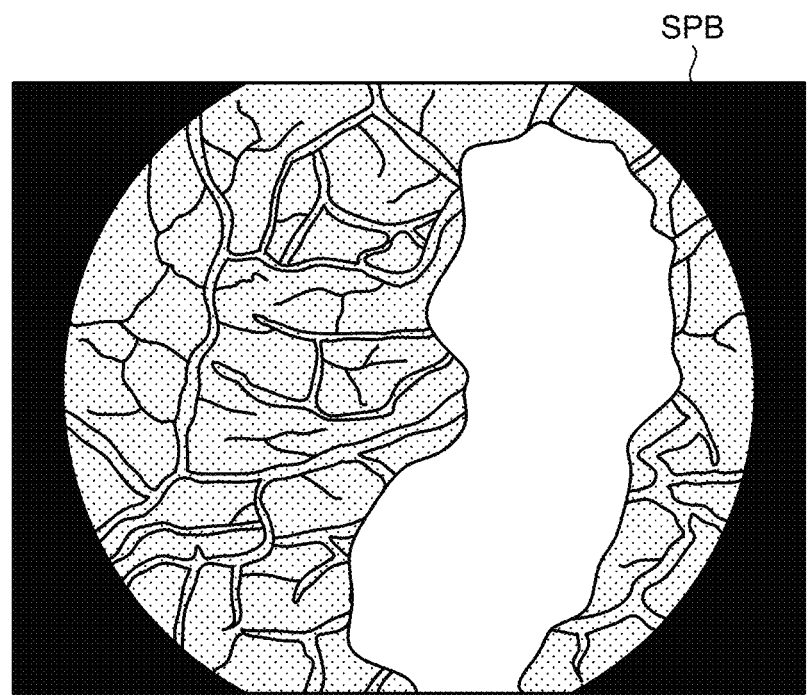
FIG. 5 is a diagram illustrating operation of a control device.
Figure 6:
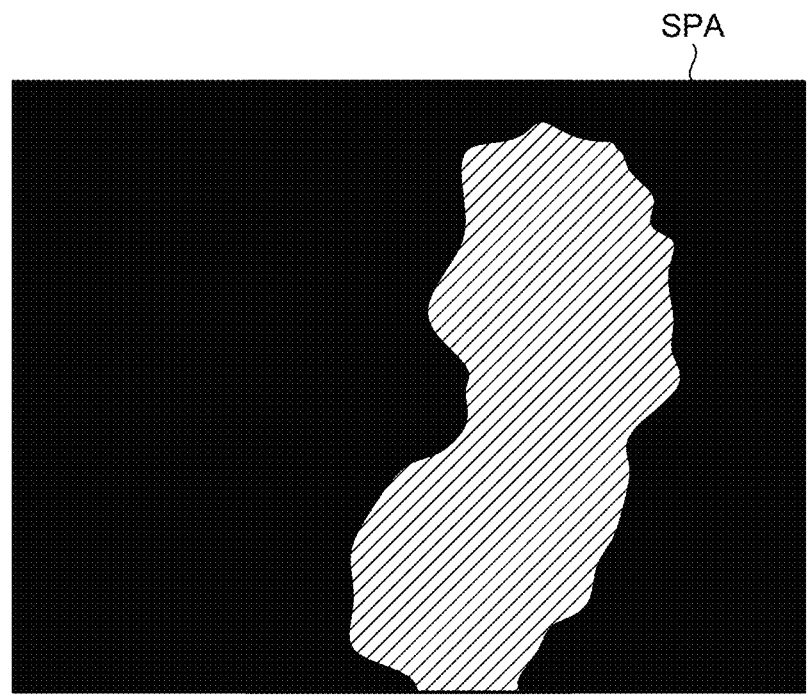
FIG. 6 is a diagram illustrating operation of a control device.
Figure 7:
FIG. 7 is a diagram illustrating operation of a control device.

FIG. 3 is a flowchart illustrating operation of the control device 9. FIGS. 4 to 7 are diagrams illustrating the operation of the control device 9. Specifically, FIG. 4 is a diagram illustrating a one-frame normal light image WLI. FIG. 5 is a diagram illustrating a one-frame PDD image SPB read from the memory 92 by the memory controller 931 and input to the second image processing unit 933. In FIG. 5, in the PDD image SPB, the area of the fluorescent component (fluorescent area) in which the protoporphyrin excited by the excitation light in the living body fluoresces is expressed in white, and the area other than the fluorescence area (excitation light component area) is expressed by a dot-hatch pattern. FIG. 6 is a diagram illustrating a PDD image SPA that has undergone the second image processing executed on a PDD image SPB. FIG. 7 is a diagram illustrating a one-frame superimposed image D1 generated by the superimposed image generator 934.

First, the light source controller 941 executes time-division drive of the first and second light sources 31 and 32 (step S1). Specifically, in step S1, the light source controller 941 controls the first light source 31 to emit light based on the synchronization signal in the first period and controls the second light source 32 to emit light in the second period, out of the first and second periods that are alternately repeated.

After step S1, based on the synchronization signal, the imaging controller 942 controls the image sensor 541 to capture the first and second subject images respectively in the first and second periods in synchronization with the light emission timings of the first and second light sources 31 and 32 (steps S2 to S4). That is, when the capturing is performed in the first period (step S2: Yes), in other words, when normal light (white light) has been emitted into the living body, the image sensor 541 captures the first subject image (normal light) and generates a normal light image (step S3). By contrast, when the capturing is performed in the second period (step S2: No), in other words, when excitation light has been emitted into the living body, the image sensor 541 captures the second subject image (excitation light and fluorescence) and generates a PDD image (step S4).

After steps S3 and S4, the memory controller 931 controls writing and reading of the captured image to and from the memory 92 based on the synchronization signal (step S5).

After step S5, the first and second image processing units 932 and 933 execute the following processes (step S6).

That is, the first image processing unit 932 sequentially executes the first image processing on each of the normal light images (for example, the normal light image WLI illustrated in FIG. 4) sequentially read from the memory 92 by the memory controller 931.

Furthermore, the second image processing unit 933 sequentially executes the second image processing on each of the PDD images (for example, the PDD image SPB illustrated in FIG. 5) sequentially read from the memory 92 by the memory controller 931. Here, the second image processing includes an adjustment process. Therefore, for example, as illustrated in FIGS. 5 and 6, after the adjustment process is executed on the PDD image SPB, a PDD image SPA in which the pixel values of the excitation light component area (represented by dots in FIG. 5) other than the fluorescence area (represented in white in FIG. 5) included in the PDD image SPB are set to "0" (represented by black in FIG. 6) is generated. Furthermore, the second image processing includes the color change process. Therefore, after the color change process is executed on the PDD image SPB, as illustrated in FIGS. 5 and 6, for example, a PDD image SPA in which the fluorescence area (represented in white in FIG. 5) included in the PDD image SPB has been changed to a specific color (represented by hatched lines in FIG. 6) is generated.

After step S6, the superimposed image generator 934 executes the superimposition process in which each of PDD images (for example, PDD image SPA illustrated in FIG. 6) output sequentially from the second image processing unit 933 is superimposed over each of the normal light images (for example, the normal light image WLI illustrated in FIG. 4) sequentially output from the first image processing unit 932 so as to generate a superimposed image (for example, a superimposed image D1 illustrated in FIG. 7) (step S7).

After step S7, the display controller 935 sequentially generates a video signal for displaying each of the superimposed images (for example, the superimposed image D1 illustrated in FIG. 7) generated sequentially by the superimposed image generator 934, and then sequentially outputs the generated video signal to the display device 7 (step S8). With this procedure, the superimposed image (for example, the superimposed image D1 illustrated in FIG. 7) is sequentially displayed on the display device 7.

After step S8, the wave detection processing unit 936 executes the wave detection process based on the pixel information for each of pixels of a specific wave detection area in the entire image area of the normal light image after the first image processing is executed in step S6 (step S9). An example of the wave detection area is an area including an image center in a normal light image. Subsequently, the wave detection processing unit 936 outputs the wave detection information obtained by the wave detection process to the control unit 94.

After step S9, the evaluation value calculation unit 943 calculates an evaluation value (in-focus evaluation value, first and second brightness evaluation values) based on the wave detection information obtained by the wave detection process in step S9 (step S10).

Specifically, in step S10, the evaluation value calculation unit 943 calculates an in-focus evaluation value for evaluating the in-focus state of the image in the wave detection area of the entire image area of the normal light image based on the wave detection information (contrast and frequency component). For example, the evaluation value calculation unit 943 sets the contrast obtained by the wave detection process in step S9 or the sum of the high frequency components among the frequency components obtained by the wave detection process in step S9, as the in-focus evaluation value. The in-focus evaluation value indicates that the larger the value, the higher focus is achieved.

Furthermore, the evaluation value calculation unit 943 calculates the first brightness evaluation value and the second brightness evaluation value in step S10.

Specifically, in step S10, based on the wave detection information (luminance mean value), the evaluation value calculation unit 943 calculates a first brightness evaluation value for changing the brightness of the image within the wave detection area among the entire image area of the normal light image, to a reference brightness (changing the wave detection information (brightness mean value) to the reference luminance mean value). Here, there is a correlation between the normal light image and the PDD image obtained by capturing the same subject at substantially the same timing. By using the correlation, the evaluation value calculation unit 943 calculates the second brightness evaluation value for changing the brightness of the PDD image to the reference brightness value, based on the above first brightness evaluation value.

Here, examples of the first brightness evaluation value include: exposure time of each of pixels in the image sensor 541 in the period of generating the normal light image; an analog gain multiplied by the signal processing unit 542 in the period of generating the normal light image; a digital gain multiplied in the first image processing (digital gain processing) performed by the first image processing unit 932, and the amount of normal light (white light) supplied by the first light source 31 in the first period.

Moreover, examples of the second brightness evaluation value include: exposure time of each of pixels in the image sensor 541 during the period for generating the PDD image; an analog gain multiplied by the signal processing unit 542 during the period for generating the PDD image; a digital gain multiplied in the second image processing (digital gain processing) performed by the second image processing unit 933, and the amount of excitation light supplied by the second light source 32 during the second period.

After step S10, the focus position controller 944 executes an AF process of adjusting the focus position of the lens unit 51 (step S11). The AF process corresponds to the first control according to the present disclosure.

Specifically, in step S11, the focus position controller 944 refers to the in-focus evaluation value calculated in step S10 and the current focus position detected by the focus position detector 53. Subsequently, the focus position controller 944 controls the operation of the lens drive unit 52 by a hill climbing technique or the like while referring to the in-focus evaluation value and the current focus position so as to position the focus lens 511 at the focus position where the image within the wave detection area out of the entire image area of the normal light image comes in an in-focus state. This allows the image in the wave detection area out of the entire image area of the normal light image to come in the in-focus state, and allows the image in the wave detection area in the entire image area of the PDD image to come in the in-focus state.

After step S11, the brightness controller 945 executes a brightness adjustment process of adjusting the brightness of the normal light image and the PDD image (step S12). The brightness adjustment process corresponds to the second control according to the present disclosure.

Specifically, when the first brightness evaluation value calculated in step S10 is "exposure time", the brightness controller 945 outputs a control signal to the imaging unit 54 and sets the exposure time of each of pixels of the image sensor 541 during the generation period of a normal light image, as the first brightness evaluation value. When the first brightness evaluation value calculated in step S10 is "analog gain", the brightness controller 945 outputs a control signal to the imaging unit 54 and sets the analog gain multiplied by the signal processing unit 542 during the generation period of a normal light image, as the first brightness evaluation value. Furthermore, when the first brightness evaluation value calculated in step S10 is "digital gain", the brightness controller 945 outputs a control signal to the observation image generator 93, and sets the digital gain multiplied by the first image processing (digital gain processing) performed by the first image processing unit 932, as the first brightness evaluation value. In addition, when the first brightness evaluation value calculated in step S10 is "the amount of normal light (white light)", the brightness controller 945 outputs a control signal to the light source device 3, and sets the amount of normal light (white light) supplied by the first light source 31 in the first period, as the first brightness evaluation value.

Similarly, when the second brightness evaluation value calculated in step S10 is "exposure time", the brightness controller 945 outputs a control signal to the imaging unit 54 and sets the exposure time of each of pixels of the image sensor 541 during the generation period of a PDD image, as the second brightness evaluation value. When the second brightness evaluation value calculated in step S10 is "analog gain", the brightness controller 945 outputs a control signal to the imaging unit 54 and sets the analog gain multiplied by the signal processing unit 542 during the generation period of a PDD image, as the second brightness evaluation value. Furthermore, when the second brightness evaluation value calculated in step S10 is "digital gain", the brightness controller 945 outputs a control signal to the observation image generator 93, and sets the digital gain multiplied by the second image processing (digital gain processing) performed by the second image processing unit 933, as the second brightness evaluation value. In addition, when the second brightness evaluation value calculated in step S10 is "the amount of excitation light", the brightness controller 945 outputs a control signal to the light source device 3, and sets the amount of excitation light supplied by the second light source 32 during the second period, as the second brightness evaluation value.

The focus position controller 944 and the brightness controller 945 described above correspond to the operation controller according to the present disclosure.

The first embodiment described above achieves the following effects.

Based on a normal light image, the control device 9 according to the first embodiment calculates an evaluation value used for the first and second controls. Subsequently, the control device 9 executes the first and second controls based on the evaluation value.

Therefore, according to the control device 9 according to the first embodiment, it is possible to calculate a more appropriate evaluation value as compared with a configuration in which the evaluation value used for the first and second controls is calculated based on the PDD image, and the first and second controls may be executed appropriately. That is, an image suitable for observation may be generated.

Furthermore, the control device 9 emits normal light from the light source device 3 in the first period and emits excitation light from the light source device 3 in the second period, out of the first and second periods that are alternately repeated. Furthermore, the control device 9 controls to capture a first subject image (normal light) in the first period to generate a normal light image, and controls to capture a second subject image (excitation light and fluorescence) in the second period to generate a PDD image. In addition, the control device 9 executes the first image processing on the normal light image, and executes the second image processing including the adjustment process on the PDD image. That is, since the excitation light component contained in the PDD image is deleted by the adjustment process, there is no need to use a known optical filter that cuts off the excitation light.

By observing the PDD image (for example, the PDD image SPA illustrated in FIG. 6) that has undergone the second image processing as well as observing the normal light image (for example, the normal light image WLI illustrated in FIG. 4) (in the first embodiment, observing the superimposed image (for example, the superimposed image D1 illustrated in FIG. 7)), the doctors or the like may recognize at which position in the living body the cancer cells corresponding to the area of the fluorescent component exist. Therefore, the control device 9 may generate an image suitable for observation.

Furthermore, by adopting a single plate type configuration having only one image sensor 541 and a configuration without using a known optical filter as the configuration of the medical observation system 1, it is possible to simplify the structure.

In the adjustment process in particular, components (G value and excitation light component (B value)) other than the fluorescent component (R value), among the R, G, and B pixel values included in the PDD image, are deleted. Furthermore, the second image processing includes the color change process.

Therefore, it is possible to emphasize and display the area of the fluorescent component (the area corresponding to the cancer cells) with respect to other areas. Therefore, the control device 9 may generate an image more suitable for observation.

Second Embodiment

Next, a second embodiment will be described.

In the following description, identical reference numerals are given to the components similar to those in the first embodiment described above, and detailed description thereof will be omitted or simplified.

In the first embodiment described above, the present disclosure is applied to the medical observation system 1 using a rigid endoscope (insertion unit 2).

By contrast, in the second embodiment, the present disclosure is applied to a medical observation system using a videoscope having an imaging unit on the distal end side of an insertion unit.

Figure 8:
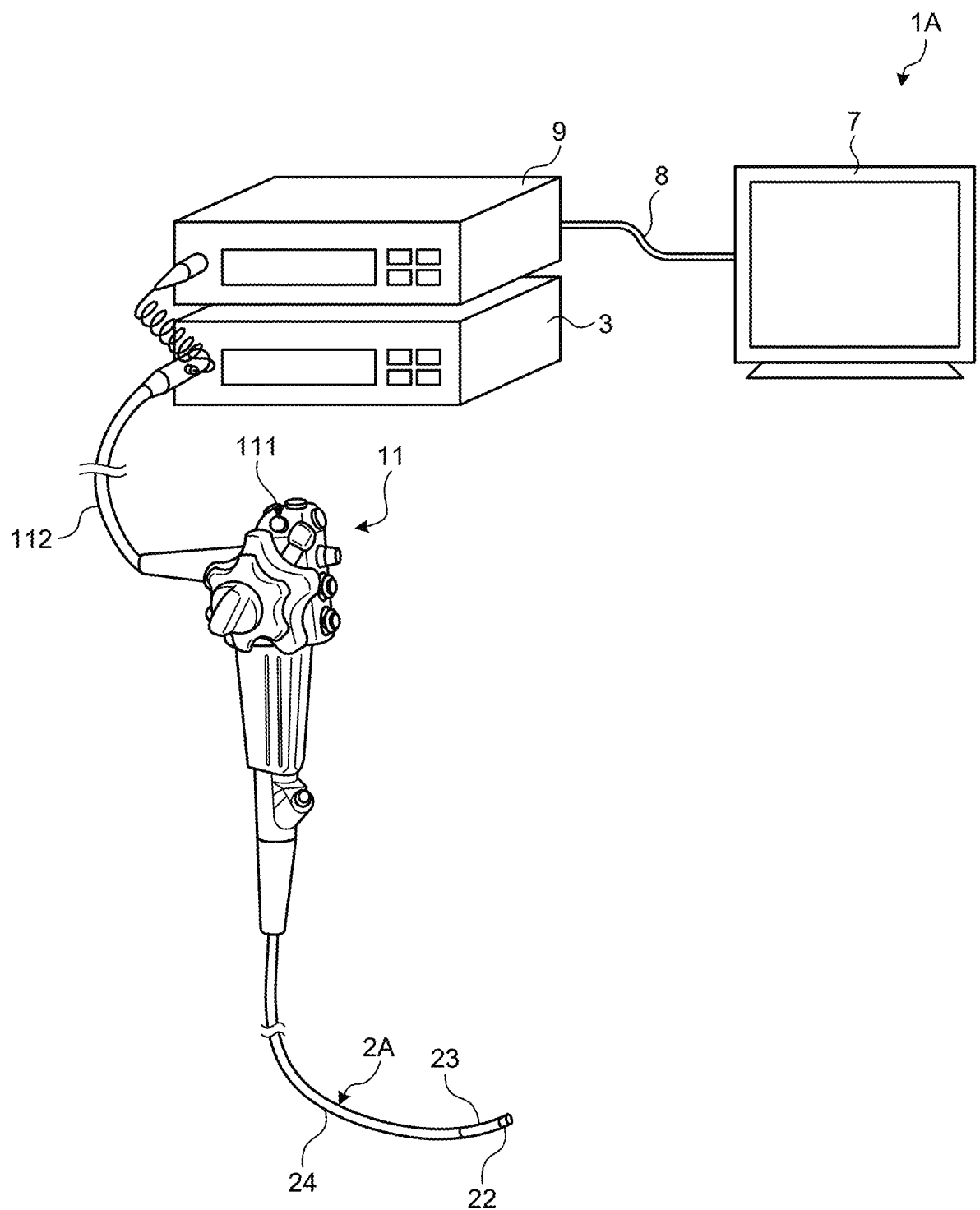
FIG. 8 is a view illustrating a configuration of a medical observation system according to a second embodiment.

FIG. 8 is a view illustrating a configuration of a medical observation system 1A according to the second embodiment.

As illustrated in FIG. 8, the medical observation system 1A according to the second embodiment includes an endoscope 11 that captures an in-vivo image of an observed region and outputs an image signal by inserting an insertion unit 2A into the living body, a light source device 3 that generates illumination light to be emitted from the distal end of the endoscope 11, a control device 9 that processes the image signal output from the endoscope 11, and a display device 7 connected to the control device 9 via a second transmission cable 8 and configured to display an image based on a video signal processed by the control device 9.

As illustrated in FIG. 8, the endoscope 11 includes an insertion unit 2A that is a flexible and elongated portion, an operating unit 111 that is connected on a proximal end of the insertion unit 2A and receives input of various operation signals, and a universal cord 112 that extends from the operating unit 111 in a direction different from the extending direction of the insertion unit 2A and incorporates various cables for connecting with the light source device 3 and the control device 9.

As illustrated in FIG. 8, the insertion unit 2A includes a distal end portion 22, a bendable portion 23 that is a bendable portion connected to the proximal end side of the distal end portion 22 and is formed with a plurality of bending pieces, and a flexible tube portion 24 that is a flexible and elongated portion connected to the proximal end side of the bendable portion 23.

Although the specific illustration is omitted, the distal end portion 22 incorporates a configuration substantially similar to that of the imaging unit 54 described in the first embodiment above. Furthermore, although the specific illustration is omitted, the operating unit 111 incorporates a configuration substantially similar to that of the communication unit 55 described in the first embodiment above. The image signal captured by the distal end portion 22 (imaging unit) is output to the control device 9 via the operating unit 111 and the universal cord 112.

Even when a flexible endoscope (endoscope 11) is used as in the second embodiment described above, the effects similar to those of the first embodiment described above may be obtained.

Third Embodiment

Next, a third embodiment will be described.

In the following description, identical reference numerals are given to the components similar to those in the first embodiment described above, and detailed description thereof will be omitted or simplified.

In the first embodiment described above, the present disclosure is applied to the medical observation system 1 using a rigid endoscope (insertion unit 2).

By contrast, in the third embodiment, the present disclosure is applied to a medical observation system using a surgical microscope that captures an enlarged image of a predetermined visual field area inside the subject (in vivo) or on the surface of the subject (living surface).

Figure 9:
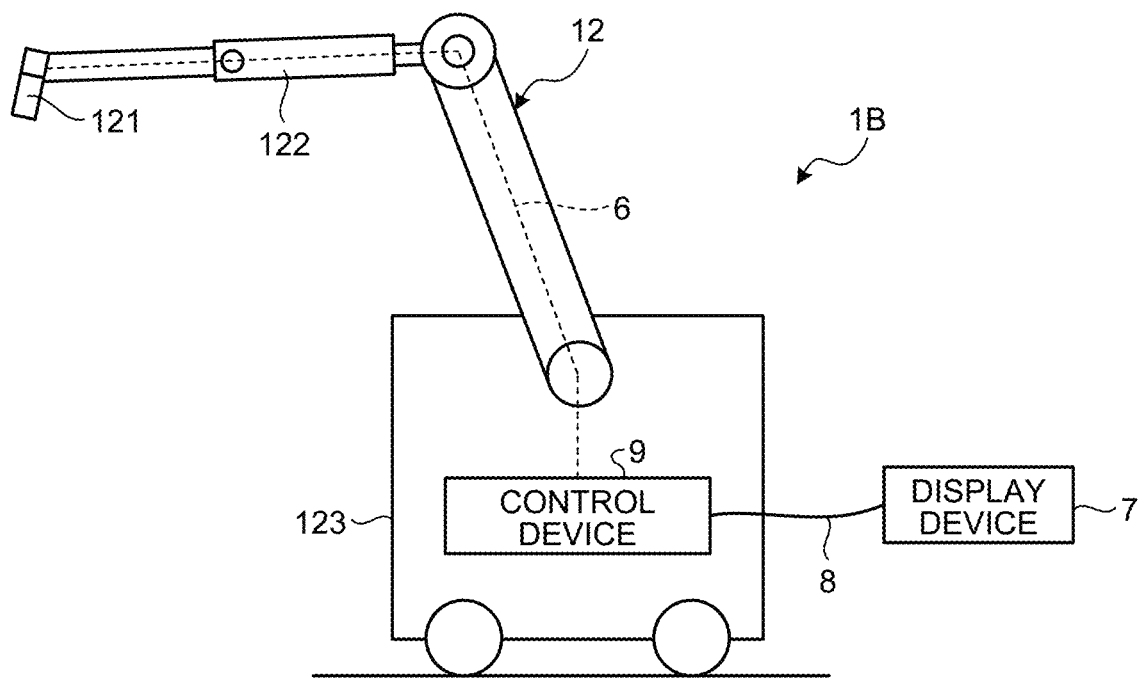
FIG. 9 is a view illustrating a configuration of a medical observation system according to a third embodiment.

FIG. 9 is a view illustrating a configuration of a medical observation system 1B according to the third embodiment.

As illustrated in FIG. 9, the medical observation system 1B according to the third embodiment includes: a surgical microscope 12 that captures an image for observing the subject and outputs an image signal, a control device 9 that processes the image signal output from the surgical microscope 12, and a display device 7 that is connected to the control device 9 via a second transmission cable 8 and displays an image based on a video signal processed by the control device 9.

As illustrated in FIG. 9, the surgical microscope 12 includes a microscope unit 121 that captures an enlarged image of the minute sites of the subject and outputs an image signal, a support 122 connected to the proximal end of the microscope unit 121 and that includes an arm that pivotably supports the microscope unit 121, and a base 123 that pivotably holds the proximal end portion of the support 122 and is movable on the floor surface.

As illustrated in FIG. 9, the control device 9 is installed in the base 123. Furthermore, although a specific illustration is omitted, a light source device 3 for generating illumination light to irradiate the subject from the surgical microscope 12 is also installed on the base 123.

The base 123 may also be fixed to the ceiling, wall surface, or the like to support the support 122, instead of being movably provided on the floor surface.

Although the specific illustration is omitted, the microscope unit 121 incorporates a configuration substantially similar to that of the imaging unit 54 and the communication unit 55 described in the first embodiment described above. The image signal captured by the microscope unit 121 (imaging unit) is output to the control device 9 via the first transmission cable 6 wired along the support 122.

Even when the surgical microscope 12 is used as in the third embodiment described above, the effects similar to those of the first embodiment described above may be obtained.

Fourth Embodiment

Next, a fourth embodiment will be described.

In the following description, identical reference numerals are given to the components similar to those in the first embodiment described above, and detailed description thereof will be omitted or simplified.

Figure 10:
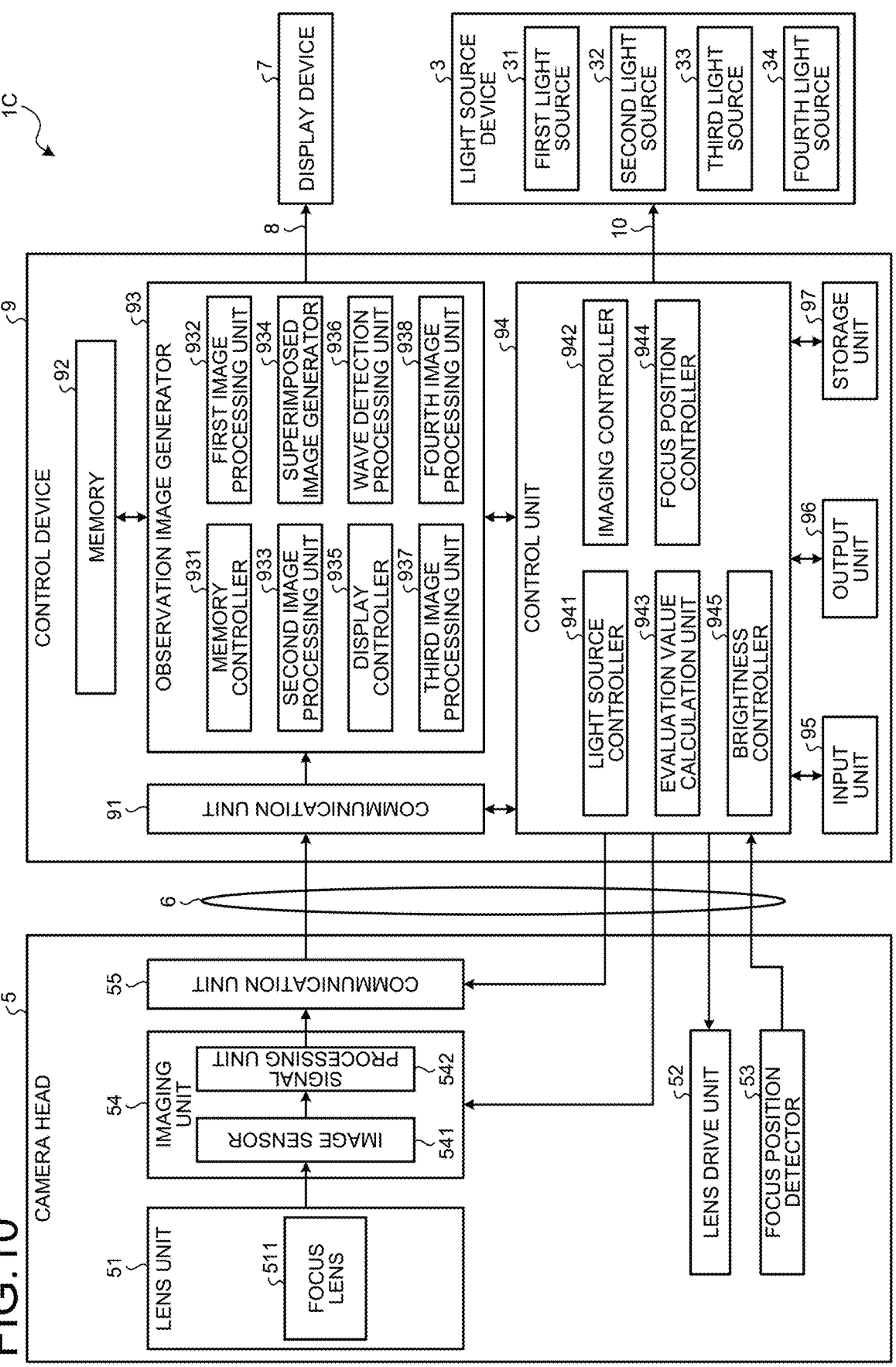
FIG. 10 is a view illustrating a configuration of a medical observation system according to a fourth embodiment.

FIG. 10 is a view illustrating a configuration of a medical observation system 1C according to the fourth embodiment.

In the medical observation system 1 according to the first embodiment described above, only two images, a normal light image and a PDD image, are generated.

By contrast, the medical observation system 1C according to the fourth embodiment is different from the medical observation system 1 in that it generates an IR image and an NBI image in addition to the normal light image and the PDD image.

Moreover, in the medical observation system 1C, as illustrated in FIG. 10, third and fourth light sources 33 and 34 have been added to the light source device 3, and third and fourth image processing units 937 and 938 have been added to the observation image generator 93, as compared with the medical observation system 1 described in the above first embodiment.

The third light source 33 emits excitation light (performs light-emission) in a third wavelength band different from the first and second wavelength bands. In the fourth embodiment, the third light source 33 emits excitation light in the near-infrared wavelength band (third wavelength band). Examples of the third light source 33 include an LED, a semiconductor laser, or the like. In order to distinguish between the excitation light emitted by the second light source 32 and the excitation light emitted by the third light source 33, hereinafter, the excitation light emitted by the second light source 32 will be referred to as PDD excitation light below, while the excitation light emitted by the third light source 33 will be referred to as IR excitation light.

In addition, the IR excitation light emitted by the third light source 33 is excitation light that excites a fluorescent substance such as indocyanine green. When excited by the IR excitation light, the fluorescent substance such as indocyanine green emits fluorescence having a center wavelength on the longer wavelength side than the center wavelength of the wavelength band of the IR excitation light. Note that the wavelength band of the IR excitation light and the wavelength band of the fluorescence may be set so as to partially overlap each other, or may be set so as not to overlap at all.

The fourth light source 34 emits light (performs light-emission) in a third wavelength band different from the first and second wavelength bands. In the fourth embodiment, the fourth light source 34 emits light (hereinafter referred to as Narrow Band Imaging (NBI) special light) that combines narrow band light, namely green light (for example, a wavelength band of 530 nm to 550 nm) and blue light (for example, a wavelength band of 390 nm to 445 nm) used for NBI observation. Examples of the fourth light source 34 include an LED, a semiconductor laser, or the like.

Under the control of the light source controller 941, the light source device 3 according to the fourth embodiment repeatedly executes light emission by using a combination of the first period, the second period, the IR period, and the NBI period, which are combined by specific time-division light emission patterns describe below.

Figure 12:
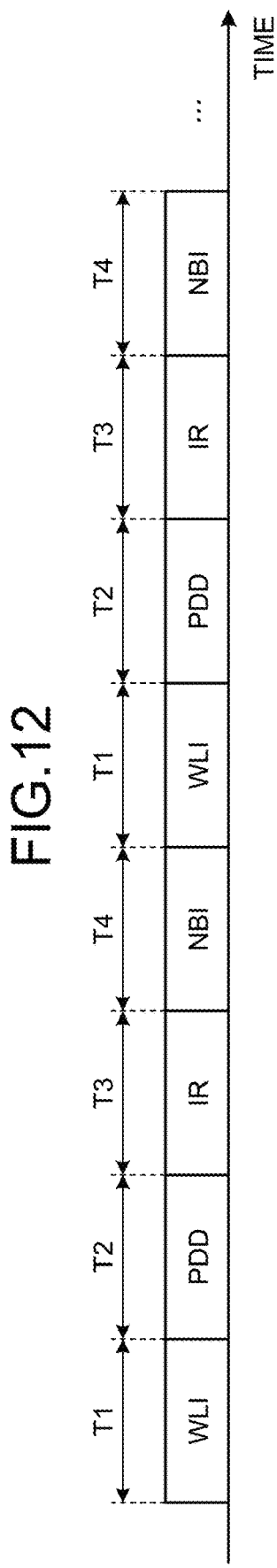
FIG. 12 is a diagram illustrating operation of a control device.

The specific time-division light emission pattern according to the fourth embodiment is a pattern in which a first period T1, a second period T2, an IR period T3, and an NBI period T4 are combined in this order (refer to FIG. 12).

In the first period T1, the first light source 31 in the light source device 3 is driven and emits normal light, similarly to the first embodiment described above.

In the second period T2, the second light source 32 of the light source device 3 is driven and emits PDD excitation light, similarly to the first embodiment described above.

The IR period T3 corresponds to a third period of the present disclosure. In this IR period T3, the third light source 33 in the light source device 3 is driven and emits IR excitation light.

The NBI period T4 corresponds to the third period of the present disclosure. In this NBI period T4, the fourth light source 34 in the light source device 3 is driven and emits NBI special light.

In the IR period T3, when the IR excitation light is supplied from the third light source 33 and then applied to the living body via the light guide 4 and the insertion unit 2, beams of the IR excitation light reflected in the living body, and the fluorescence emitted from the excited fluorescent substance such as indocyanine green accumulated in the lesion in the living body, are collected into the insertion unit 2. In the following, for convenience of explanation, the IR excitation light and fluorescence collected by the optical system in the insertion unit 2 will be referred to as an IR subject image.

In the NBI period T4, when the NBI special light is emitted into the living body through the light guide 4 and the insertion unit 2 supplied from the fourth light source 34, the NBI special light reflected in the living body is collected by the optical system in the insertion unit 2. In the following, for convenience of explanation, the NBI special light collected by the optical system in the insertion unit 2 will be referred to as an NBI subject image.

Subsequently, the image sensor 541 according to the fourth embodiment performs capturing for each of the first and second periods T1 and T2, IR period T3, and NBI period T4 under the control of the imaging controller 942. In the IR period T3, the image sensor 541 generates an IR image (corresponding to a third captured image according to the present disclosure) by capturing an IR subject image (IR excitation light and fluorescence). Furthermore, in the NBI period T4, the image sensor 541 generates an NBI image (corresponding to the third captured image according to the present disclosure) by capturing an NBI subject image (NBI special light).

The third image processing unit 937 executes image processing (hereinafter referred to as IR image processing) different from the first and second image processing, on the input IR image (RAW signal (digital signal)).

Similarly to the first and second image processing as above, examples of the IR image processing includes optical black subtraction processing, a white balance adjustment process, digital gain processing, demosaic processing, color correction matrix processing, gamma correction processing, YC processing of converting RGB signals (IR images) into a luminance signal and color difference signals (Y, CB/CR signals), or the like.

The fourth image processing unit 938 executes image processing (hereinafter, NBI image processing) different from the first and second image processing or IR image processing, on the input NBI image (RAW signal (digital signal)).

Similarly to the first and second image processing and the IR image processing as above, examples of the NBI image processing includes optical black subtraction processing, a white balance adjustment processing, digital gain processing, demosaic processing, color correction matrix processing, gamma correction processing, YC processing of converting RGB signals (NBI image) into a luminance signal and color difference signals (Y, CB/CR signals), or the like.

Next, operation of the control device 9 according to the fourth embodiment will be described.

Figure 11:
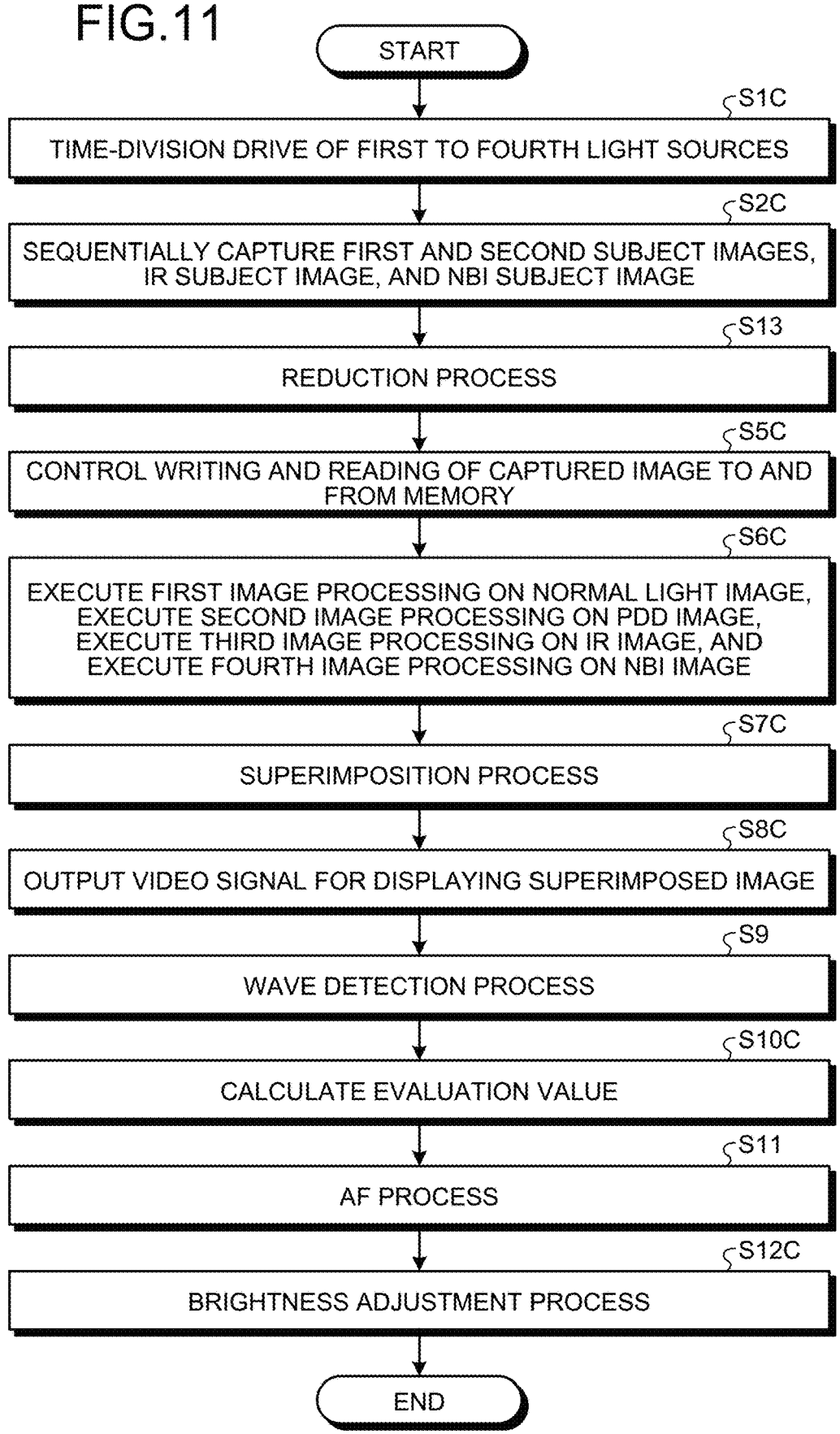
FIG. 11 is a flowchart illustrating operation of a control device.
Figure 13:
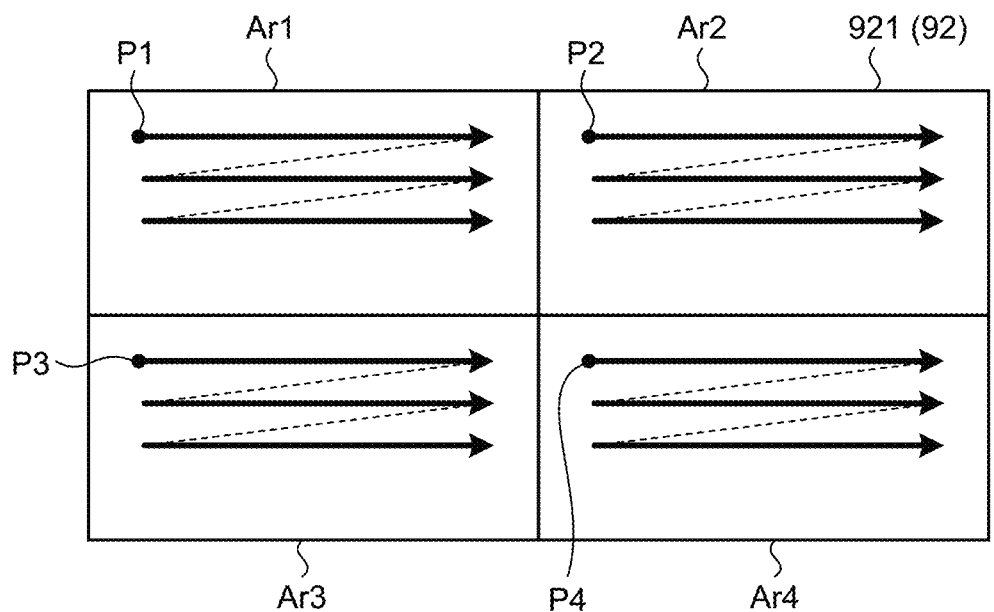
FIG. 13 is a diagram illustrating operation of a control device.
Figure 14:
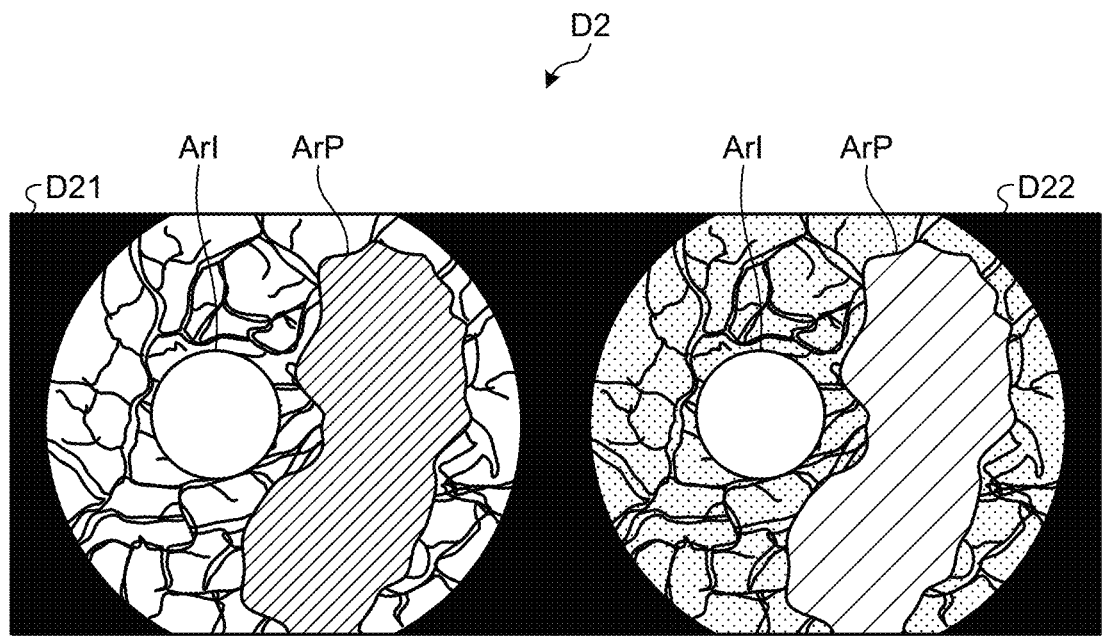
FIG. 14 is a diagram illustrating operation of a control device.

FIG. 11 is a flowchart illustrating operation of the control device 9. FIGS. 12 to 15 are diagrams illustrating operations of the control device 9. Specifically, FIG. 12 is a time chart illustrating the light emission timings of the first to fourth light sources 31 to 34. In FIG. 12, for convenience of explanation, the letters "WLI" representing normal light are illustrated in the first period T1; the letters "PDD" representing the PDD excitation light are illustrated in the second period T2; the letters "IR" representing the IR excitation light are illustrated in the IR period T3; and the letters "NBI" representing the NBI special light are illustrated in the NBI period T4. FIG. 13 is a diagram illustrating the operation of the memory controller 931. Note that FIG. 13 schematically illustrates a specific bank 921 among a plurality of banks in the memory 92. In the fourth embodiment, the bank 921 has a memory capacity corresponding to the amount of data of an image having 4K pixel resolution. Furthermore, in FIG. 13, the entire area of the bank 921 is evenly divided into four areas, namely, first to fourth divided areas Ar1 to Ar4 in a quadrisected-square shape. That is, in the fourth embodiment, the first to fourth divided areas Ar1 to Ar4 have a memory capacity corresponding to the amount of data of an image having a full HD pixel resolution. FIG. 14 is an example of a display image D2 displayed on the display device 7.

In the following, it is assumed that the image sensor 541 is an image sensor that generates images each having 4K pixel resolution (normal light image, PDD image, IR image, and NBI image), individually. Furthermore, it is assumed that the maximum amount of data that may be processed by the first image processing unit 932 is the amount of data of an image having a full HD pixel resolution. The similar applies to the other units, namely, the second to fourth image processing units 933, 937, and 938.

First, the light source controller 941 executes time-division drive of the first to fourth light sources 31 to 34 (step S1C). Specifically, as illustrated in FIG. 12, the light source controller 941 controls in step S1D light emission based on the synchronization signal, specifically controls the first light source 31 to emit light in the first period T1, controls the second light source 32 to emit light in the second period T2, controls the third light source 33 to emit light in the IR period T3, and controls the fourth light source 34 to emit light in the NBI period T4.

After step S1C, based on the synchronization signal, the imaging controller 942 controls the image sensor 541 to capture the first subject image, the second subject image, the IR subject image, and the NBI subject image, respectively in the first period T1, the second period T2, the IR period T3, and the NBI period T4 in synchronization with the light emission timings of the first and fourth light sources 31 and 34 (step S2C). That is, when the capturing is performed in the first period T1, in other words, when normal light (white light) is emitted into the living body, the image sensor 541 captures the first subject image (normal light) and generates a normal light image. Moreover, when the capturing is performed in the second period T2, in other words, when PDD excitation light is emitted into the living body, the image sensor 541 captures the second subject image (PDD excitation light and fluorescence) and generates a PDD image. Furthermore, when the capturing is performed in the IR period T3, in other words, when IR excitation light is emitted into the living body, the image sensor 541 captures the IR subject image (IR excitation light and fluorescence) and generates an IR image. In addition, when the capturing is performed in the NBI period T4, in other words, when NBI special light is emitted into the living body, the image sensor 541 captures the NBI subject image (NBI special light) and generates an NBI image.

After step S2C, the signal processing unit 542 executes a reduction process (step S13). By the reduction process, the normal light image, PDD image, IR image, and NBI image having 4K pixel resolution are respectively converted into a normal light image, PDD image, IR image, and NBI image having full HD pixel resolution. The imaging unit 54 sequentially outputs the normal light image, PDD image, IR image, and NBI image having the full HD pixel resolution in raster units.

After step S13, the memory controller 931 controls writing an image to the memory 92 and reading an image from the memory 92 (step S5C).

Specifically, as illustrated by arrows and broken lines in FIG. 13, the memory controller 931 sequentially writes the normal light images (pixel resolution: full HD) in raster units, which have been sequentially output from the imaging unit 54 and received by the communication unit 91, to the first divided area Ar1 in the bank 921, on the line-by-line basis. After writing one frame of a normal light image (pixel resolution: full HD) to the first divided area Ar1, the memory controller 931 then sequentially writes the PDD images (pixel resolution: full HD) in raster units, which have been sequentially output from the imaging unit 54 and received by the communication unit 91, to the second divided area Ar2 in the bank 921, on the line-by-line basis. Furthermore, after writing one frame of a PDD image (pixel resolution: full HD) to the second divided area Ar2, the memory controller 931 then sequentially writes the IR images (pixel resolution: full HD) in raster units, which have been sequentially output from the imaging unit 54 and received by the communication unit 91, to the third divided area Ar3 in the bank 921, on the line-by-line basis. Furthermore, after writing one frame of an IR image (pixel resolution: full HD) to the third divided area Ar3, the memory controller 931 then sequentially writes the NBI images (pixel resolution: full HD) in raster units, which have been sequentially output from the imaging unit 54 and received by the communication unit 91, to the fourth divided area Ar4 in the bank 921, on the line-by-line basis.

In addition, the memory controller 931 sequentially reads the normal light image (pixel resolution: full HD), the PDD image (pixel resolution: full HD), the IR image (pixel resolution: full HD), and the NBI image (pixel resolution: full HD) which have been written in the first to fourth divided areas Ar1 to Ar4 from the first to fourth storage positions P1 to P4 on the line-by-line basis, at substantially the same timing as the timing when the NBI image is started to be written from the fourth storage position P4.

Here, the pixel data stored in the first storage position P1 is pixel data regarding the pixel at the upper left corner position in the normal light image (pixel resolution: full HD). The pixel data stored in the second storage position P2 is pixel data regarding the pixel at the upper left corner position in the PDD image (pixel resolution: full HD). The pixel data stored in the third storage position P3 is pixel data regarding the pixel at the upper left corner position in the IR image (pixel resolution: full HD). The pixel data stored in the fourth storage position P4 is pixel data regarding the pixel at the upper left corner position in the NBI image (pixel resolution: full HD).

Subsequently, the read normal light image (pixel resolution: full HD) is sequentially input to the first image processing unit 932 on the line-by-line basis. The read PDD image (pixel resolution: full HD) is sequentially input to the second image processing unit 933 on the line-by-line basis. The read IR image (pixel resolution: full HD) is sequentially input to the third image processing unit 937 on the line-by-line basis. The read NBI image (pixel resolution: full HD) is sequentially input to the fourth image processing unit 938 on the line-by-line basis.

After step S5C, the first to fourth image processing units 932, 933, 937, and 938 execute image processing in parallel onto the input images, namely, the normal light image (pixel resolution: full HD), the PDD image (pixel resolution: full HD), the IR image (pixel resolution: full HD), and the NBI image (pixel resolution: full HD) (step S6C). Here, the first image processing unit 932 executes the first image processing on the input normal light image (pixel resolution: full HD). In addition, the second image processing unit 933 executes the second image processing (including the adjustment process and color change process) on the input PDD image (pixel resolution: full HD). The third image processing unit 937 executes the third image processing on the input IR image (pixel resolution: full HD). The fourth image processing unit 938 executes the fourth image processing on the input NBI image (pixel resolution: full HD).

After step S6C, the superimposed image generator 934 generates a superimposed image by executing a superimposition process onto each of normal light images sequentially output from the first image processing unit 932, each of PDD images sequentially output from the second image processing unit 933, each of IR images sequentially output from the third image processing unit 937, and each of NBI images sequentially output from the fourth image processing unit 938 (step S7C).

Examples of the superimposed image include a first superimposed image D21 (FIG. 14) in which a PDD image and an IR image are superimposed over a normal light image, and a second superimposed image D22 (FIG. 14) in which a PDD image and an IR image are superimposed over an NBI image.

Furthermore, the superimposition process includes a first superimposition process and a second superimposition process illustrated below, as an example. Hereinafter, in a PDD image, an area formed with pixels having a luminance value of a specific threshold or more will be referred to as a PDD fluorescence area. Furthermore, in an IR image, an area formed with pixels having a luminance value of a specific threshold or more will be referred to as an IR fluorescence area.

The first superimposition process is a process of replacing an area having the same pixel position as the PDD fluorescence area and the IR fluorescence area in the normal light image or the NBI image, with an image of the PDD fluorescence area and the IR fluorescence area in the PDD image and the IR image.

The second superimposition process is a process of changing the brightness of the color indicating fluorescence to be given to each of pixels in the area having the same pixel position as the PDD fluorescence area and the IR fluorescence area in a normal light image or an NBI image, based on the luminance value of each of the pixel positions in the PDD fluorescence area and the IR fluorescence area of the PDD image and the IR image.

After step S7C, the display controller 935 sequentially generates a video signal for displaying each of the superimposed images generated sequentially by the superimposed image generator 934, and then sequentially outputs the generated video signal to the display device 7 (step S8C).

With this procedure, the superimposed image is sequentially displayed on the display device 7.

For example, the display device 7 displays a display image D2 illustrated in FIG. 14.

Specifically, as illustrated in FIG. 14, the display image D2 is an image in which the first superimposed image D21 and the second superimposed image D22 are arranged side by side, in which the display controller 935 executes an enlargement process on the first and the second superimposed images D21 and D22 (pixel resolution: full HD) generated by the superimposed image generator 934, leading to generation of an entire image having 4K pixel resolution. In FIG. 14, the hatched areas are the PDD fluorescence areas ArP. The blank areas are the IR fluorescence areas ArI.

After step S8C, the control device 9 executes step S9 described in the embodiment above.

After step S9, the evaluation value calculation unit 943 calculates evaluation values (in-focus evaluation value, first to fourth brightness evaluation values) based on the wave detection information obtained by the wave detection process in step S9 (step S10C).

Specifically, the evaluation value calculation unit 943 calculates the in-focus evaluation value in step S10C similarly to step S10 of the first embodiment described above.

In step S10C, the evaluation value calculation unit 943 also calculates the third and fourth brightness evaluation values in addition to the first and second brightness evaluation values described in step S10 of the first embodiment described above.

Specifically, there is a correlation between the normal light image, the IR image, and the NBI image obtained by capturing the same subject at substantially the same timing, By using the correlation, the evaluation value calculation unit 943 calculates the third brightness evaluation value for changing the brightness of the IR image to the reference brightness, and the fourth brightness evaluation value for changing the brightness of the NBI image to the reference brightness, based on the first brightness evaluation value.

Here, examples of the third brightness evaluation value include: exposure time of each of pixels in the image sensor 541 during the generation period of the IR image; an analog gain multiplied by the signal processing unit 542 during the generation period of the IR image; a digital gain multiplied in the third image processing (digital gain processing) performed by the third image processing unit 937, and the amount of IR excitation light supplied by the third light source 33 during the IR period T3.

Moreover, examples of the fourth brightness evaluation value include: exposure time of each of pixels in the image sensor 541 during the generation period of the NBI image; an analog gain multiplied by the signal processing unit 542 during the generation period of the NBI image; a digital gain multiplied in the fourth image processing (digital gain processing) performed by the fourth image processing unit 938, and the amount of NBI special light supplied by the fourth light source 34 during the NBI period T4.

After step S10C, the control device 9 executes step S11 described in the first embodiment above. With this procedure, the images in the wave detection area out of the entire image areas of the normal light image, the PDD image, the IR image, and the NBI image are in the in-focus state.

After step S11, similarly to step S12 described in the first embodiment above, the brightness controller 945 executes the first brightness adjustment process of adjusting the brightness of the normal light image and the PDD image together with the second brightness adjustment process of adjusting the brightness of the IR image and the NBI image (step S12C). The first and second brightness adjustment processes correspond to the second control according to the present disclosure.

Specifically, the second brightness adjustment process includes the following processes.

When the third brightness evaluation value calculated in step S10C is "exposure time", the brightness controller 945 outputs a control signal to the imaging unit 54 and sets the exposure time of each of pixels of the image sensor 541 during the generation period of an IR image, as the third brightness evaluation value. When the third brightness evaluation value calculated in step S10C is "analog gain", the brightness controller 945 outputs a control signal to the imaging unit 54 and sets the analog gain multiplied by the signal processing unit 542 during the generation period of an IR image, as the third brightness evaluation value. Furthermore, when the third brightness evaluation value calculated in step S10C is "digital gain", the brightness controller 945 outputs a control signal to the observation image generator 93, and sets the digital gain multiplied by the third image processing (digital gain processing) performed by the third image processing unit 937, as the third brightness evaluation value. In addition, when the third brightness evaluation value calculated in step S10C is "the amount of IR excitation light", the brightness controller 945 outputs a control signal to the light source device 3, and sets the amount of IR excitation light supplied by the third light source 33 during the IR period T3, as the third brightness evaluation value.

Similarly, when the fourth brightness evaluation value calculated in step S10C is "exposure time", the brightness controller 945 outputs a control signal to the imaging unit 54 and sets the exposure time of each of pixels of the image sensor 541 during the generation period of an NBI image, as the fourth brightness evaluation value. When the fourth brightness evaluation value calculated in step S10C is "analog gain", the brightness controller 945 outputs a control signal to the imaging unit 54 and sets the analog gain multiplied by the signal processing unit 542 during the generation period of an NBI image, as the fourth brightness evaluation value. Furthermore, when the fourth brightness evaluation value calculated in step S10C is "digital gain", the brightness controller 945 outputs a control signal to the observation image generator 93, and sets the digital gain multiplied by the fourth image processing (digital gain processing) performed by the fourth image processing unit 938, as the fourth brightness evaluation value. Furthermore, when the fourth brightness evaluation value calculated in step S10C is "the amount of NBI special light", the brightness controller 945 outputs a control signal to the light source device 3, and sets the amount of NBI special light supplied by the fourth light source 34 during the NBI period T4, as the fourth brightness evaluation value.

According to the fourth embodiment described above, the following effects are obtained in addition to the effects similar to the case of the first embodiment described above.

The control device 9 according to the fourth embodiment repeatedly executes light emission by using a combination of the first and second periods T1, T2, IR period T3, and NBI period T4 in a specific time-division light emission pattern. Furthermore, the control device 9 controls to capture the first subject image (normal light) in the first period T1 to generate a normal light image, controls to capture the second subject image (PDD excitation light and the fluorescence) in the second period T2 to generate a PDD image, controls to capture the IR subject image (IR excitation light and fluorescence) in the IR period T3 to generate an IR image, and controls to capture the NBI subject image (NBI excitation light and fluorescence) in the NBI period T4 to generate an NBI image.

This makes it possible to simultaneously perform various types of observation (fluorescence observation using protoporphyrin, fluorescence observation using indocyanine green, and NBI observation) by using normal light images, PDD images, IR images, and NBI images. In addition, since the evaluation value is calculated based on the normal light images and the first and second controls may be appropriately executed, all of the normal light image, PDD image, IR image, and NBI image will be suitable for observation, making it possible to perform various types of observation satisfactorily.

Fifth Embodiment

Next, a fifth embodiment will be described.

In the following description, identical reference numerals are given to the components similar to those in the first embodiment described above, and detailed description thereof will be omitted or simplified.

Figure 15:
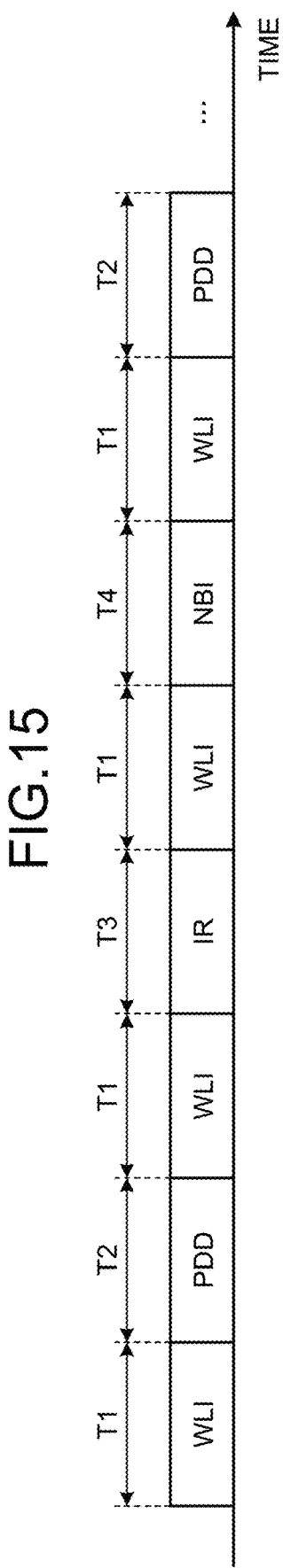
FIG. 15 is a time chart illustrating light emission timings of first to fourth light sources according to a fifth embodiment.

FIG. 15 is a time chart illustrating light emission timings of the first to fourth light sources 31 to 34 according to the fifth embodiment.

In the fifth embodiment, as illustrated in FIG. 15, the time-division light emission pattern is different from the pattern of the fourth embodiment described above.

Specifically, as illustrated in FIG. 15, the time-division light emission pattern according to the fifth embodiment is a pattern in which a first period T1, a second period T2, a first period T1, an IR period T3, and a first period T1, and an NBI period T4 are combined in this order. That is, the time-division light emission pattern is a pattern in which the periods are combined so that the number of the first periods T1 (three) is more than the number of the second periods T2 (one), the number of the IR periods T3 (one), and the number of the NBI periods T4 (one). Furthermore, the time-division light emission pattern is a pattern in which the periods are combined to arrange the first period T1 so as not to allow the second period T2, the IR period T3, and the NBI period T4 to be adjacent to each other.

According to the fifth embodiment described above, the following effects are obtained in addition to the effects similar to the case of the fourth embodiment described above.

The time-division light emission pattern according to the fifth embodiment is a pattern in which the periods are combined so that the number of the first periods T1 is more than the number of the second periods T2, the number of the IR periods T3, and the number of the NBI periods T4. That is, there is an increased frequency of calculating the evaluation value based on the normal light image. Furthermore, the time-division light emission pattern is a pattern in which the periods are combined to arrange the first period T1 so as not to allow the second period T2, the IR period T3, and the NBI period T4 to be adjacent to each other. That is, the normal light image for calculating the evaluation value is generated in a state of being temporally close to each of the PDD image, IR image, and NBI image.

Therefore, the evaluation values may be calculated based on the normal light images generated in a state of being temporally close to each of the PDD image, IR image, and NBI image, and the first and second controls may be executed by using the evaluation values, making it possible to improve the accuracy of the first and second controls. That is, normal light images, PDD images, IR images, and NBI images may be images more suitable for observation.

OTHER EMBODIMENTS

Embodiments of the present disclosure have been described hereinabove, however, the present disclosure is not intended to be limited to the above-described first to fifth embodiments.

Although the above-described first to fifth embodiments are cases where the control device 9 calculates the evaluation values used for the first and second controls based on the normal light image, the present disclosure is not limited to this calculation method. The medical image processing apparatus according to the present disclosure may have a configuration in which only the evaluation value of one of the first and second controls is calculated, for example, as long as at least one of the evaluation values of the first and second controls is calculated based on the normal light image.

While the above-described first to third embodiments are cases where the light in the first wavelength band and the excitation light in the second wavelength band are emitted in time-division, the present disclosure is not limited to this procedure. For example, it is allowable to use a configuration in which the light in the first wavelength band and the excitation light in the second wavelength band are emitted at the same time, and the light in the first wavelength band, and the excitation light and fluorescence in the second wavelength band, are separated from each other by a filter on the capturing side, then, capturing is performed individually by two image sensors.

The above-described first to third embodiments are cases where the light source device 3 may emit white light as normal light in the first wavelength band and may emit light in the blue wavelength band as excitation light in the second wavelength band. The present disclosure is not limited to this, and other types of light may be adopted as the normal light in the first wavelength band and the excitation light in the second wavelength band, individually. At this time, the first and second wavelength bands may be partially overlapped bands or may be completely non-overlapping bands.

In the above-described first to third embodiments, the first and second periods are set to be repeated alternately. The present disclosure is not limited to this, and at least one of the first and second periods may be set continuously and the frequency ratio of the first and second periods may be a ratio other than 1:1.

In the above-described first to third embodiments, the superimposed image is displayed on the display device 7. The present disclosure is not limited to this, and at least two of the three images, namely, the normal light image, the PDD image, and the superimposed image, may be displayed simultaneously. Furthermore, a plurality of display devices 7 may be provided, and at least two images of the three images may be simultaneously displayed on different display devices 7.

Furthermore, although the first superimposed image D21 and the second superimposed image D22 are similarly displayed on the display device 7 in the above-described fourth and fifth embodiments, the present disclosure is not limited to this display mode. For example, a normal light image, a PDD image, an IR image, and an NBI image may be displayed simultaneously. Furthermore, the first superimposed image D21 and the NBI image may be displayed at the same time. The normal light image and the second superimposed image D22 may be displayed at the same time. Furthermore, it is allowable to adopt a configuration in which a plurality of display devices 7 are provided and different images are simultaneously displayed on different display devices 7.

In the above-described fourth and fifth embodiments, the IR image and the NBI image are generated in addition to the normal light image and the PDD image. The present disclosure is not limited to this, and it is allowable to suppress generation of one of the IR image and the NBI image.

In the above-described fourth and fifth embodiments, the order of the first period T1, the second period T2, the IR period T3, and the NBI period T4 in the time-division light emission pattern is not limited to the order described in the above-described fourth and fifth embodiments, and may be other order. Furthermore, in the time-division light emission pattern of the above-described fifth embodiment, the numbers of the first periods T1, the second periods T2, the IR periods T3, and the NBI periods T4 are not limited to the numbers described in the above fifth embodiment and may be other numbers.

The above-described fourth and fifth embodiments are cases where the image sensor 541 is formed with an image sensor that generates an image having a pixel resolution of 4K. The present disclosure, however, is not limited to this, and may use an image sensor that generates an image of other pixel resolutions.

The configurations described in the above fourth and fifth embodiments may be adopted for the medical observation systems 1A and 1B respectively described in the above second and third embodiments.

In the above-described first, fourth, and fifth embodiments, a part of the camera head 5 and a part of the control device 9 may be provided in the connector CN1 or the connector CN2, for example.

The following configurations also belong to the technical scope of the present disclosure.

(1) A medical image processing apparatus including:
    a captured image acquisition unit configured to acquire a first captured image obtained by capturing light from an observation target to which light of a first wavelength band is emitted and a second captured image obtained by capturing fluorescence from the observation target excited by excitation light of a second wavelength band different from the first wavelength band;
    an evaluation value calculation unit configured to calculate, based on the first captured image, an evaluation value to be used for at least one of a first control of controlling a focus position of an imaging device configured to generate each of the first captured image and the second captured image and a second control of controlling a brightness of the first captured image and the second captured image; and
    an operation controller configured to execute at least one of the first control and the second control based on the evaluation value.

(2) The medical image processing apparatus according to (1), wherein the excitation light is light in a blue wavelength band that excites protoporphyrin.

(3) The medical image processing apparatus according to (1) or (2), further including:
    a light source controller configured to
        control a light source device to emit light in the first wavelength band from the light source device in a first period, and
        control the light source device to emit the excitation light from the light source device in a second period, the first period and the second period being alternately repeated; and an imaging controller configured to control the imaging device to capture the light from the observation target to which the light in the first wavelength band is emitted in the first period so as to generate the first captured image, and control the imaging device to capture the fluorescence from the observation target excited by the excitation light in the second period so as to generate the second captured image.

(4) The medical image processing apparatus according to (1) or (2), further including:

a light source controller configured to repeatedly execute light emission in which a first period of emitting light in the first wavelength band from a light source device, a second period of emitting the excitation light from the light source device, and a third period of emitting light in a third wavelength band different from the first wavelength band or the second wavelength band from the light source device, are combined with each other in a specific time-division light emission pattern; and an imaging controller configured to control the imaging device to capture the light from the observation target to which the light in the first wavelength band is emitted in the first period so as to generate the first captured image, control the imaging device to capture the fluorescence from the observation target excited by the excitation light in the second period so as to generate the second captured image, and control the imaging device to capture the light from the observation target to which the light in the third wavelength band is emitted in the third period so as to generate a third captured image.

(5) The medical image processing apparatus according to (4), wherein the second control includes a control of brightness of the first captured image, the second captured image, and the third captured image.

(6) The medical image processing apparatus according to (4) or (5), wherein the specific time-division light emission pattern uses a combination of the periods so that the number of the first period is to be larger than the number of the second period and the number of the third period.

(7) The medical image processing apparatus according to (6), wherein the specific time-division light emission pattern uses a combination of the periods in which the first period is arranged so as not to allow the second period and the third period to be adjacent to each other in time series.

(8) The medical image processing apparatus according to any one of (4) to (7), wherein the light in the third wavelength band is light in a near-infrared wavelength band that excites indocyanine green.

(9) The medical image processing apparatus according to any one of (4) to (8), wherein the light in the third wavelength band is light obtained by combining light in a green wavelength band and light in a blue wavelength band.

(10) A medical observation system including:

a light source device configured to emit light in a first wavelength band and excitation light in a second wavelength band different from the first wavelength band;

an imaging device configured to generate a first captured image by capturing light from an observation target to which light in the first wavelength band is emitted and that generates a second captured image by capturing fluorescence from the observation target excited by the excitation light; and a medical image processing apparatus configured to process the first captured image and the second captured image, wherein the medical image processing apparatus includes:

a captured image acquisition unit configured to acquire the first captured image and the second captured image;

an evaluation value calculation unit configured to calculate, based on the first captured image, an evaluation value to be used for at least one of a first control of controlling a focus position of the imaging device that generates the first captured image and the second captured image individually and a second control of controlling a brightness of the first captured image and the second captured image; and an operation controller configured to execute at least one of the first control and the second control based on the evaluation value.

According to the medical image processing apparatus and the medical observation system according to the present disclosure, it is possible to generate an image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing apparatus comprising:

a captured image acquisition circuit configured to acquire a first captured image obtained by capturing light from an observation target to which light of a first wavelength band is emitted and a second captured image obtained by capturing fluorescence from the observation target excited by excitation light of a second wavelength band different from the first wavelength band;

an evaluation value calculation circuit configured to calculate a focus evaluation value, based only on the first captured image, to be used for controlling a focus position of an image sensor configured to generate each of the first captured image and the second captured image, and a brightness evaluation value relating to at least one of an exposure time, a gain for image generation, a gain for image processing and an amount of a light by a light source, based on the first captured image, to be used for controlling a brightness of the first captured image and a brightness of the second captured image; and an operation control circuit configured to:

control the focus position of the image sensor based on the focus evaluation value to generate both the first captured image and the second captured image; and adjust the brightness of the first captured image based on the brightness evaluation value, and adjust the brightness of the second captured image based on a correlation between the first captured image and the second captured image, and the brightness evaluation value.

2. The medical image processing apparatus according to claim 1, wherein the excitation light is light in a blue wavelength band that excites protoporphyrin.

3. The medical image processing apparatus according to claim 1, further comprising:
a light source control circuit configured to
control a light source device to emit light in the first wavelength band from the light source device in a first period, and
control the light source device to emit the excitation light from the light source device in a second period, the first period and the second period being alternately repeated; and
an imaging control circuit configured to
control the image sensor to capture the light from the observation target to which the light in the first wavelength band is emitted in the first period so as to generate the first captured image, and
control the image sensor to capture the fluorescence from the observation target excited by the excitation light in the second period so as to generate the second captured image.

4. The medical image processing apparatus according to claim 1, further comprising an image generation circuit configured to superimpose the second captured image on the first captured image.

5. The medical image processing apparatus according to claim 4, wherein, to superimpose the second captured image, the image generation circuit is configured to replace an area in the first captured image with the second captured image.

6. The medical image processing apparatus according to claim 5, wherein the image generation circuit is further configured to, after the area in the first captured image is replaced with the second capture image, change the brightness of the color indicating fluorescence given to each of pixels in the area having the same pixel position as the first captured image in accordance with the luminance value of each of the pixel positions in the fluorescence area of the second captured image.

7. The medical image processing apparatus according to claim 1, an image generation circuit configured to delete the second wavelength band from the second captured image, wherein the second captured image includes the second wavelength band.

8. The medical image processing apparatus according to claim 1, wherein the second captured image is obtained by capturing fluorescence of visible wavelength.

9. The medical image processing apparatus according to claim 8, wherein the second captured image is obtained by capturing fluorescence of red wavelength band.

10. The medical image processing apparatus according to claim 1, wherein the second captured image is obtained by capturing fluorescence of non-visible wavelength.

11. The medical image processing apparatus according to claim 10, wherein the second captured image is obtained by capturing fluorescence of IR wavelength band.

12. A medical image processing apparatus comprising:
a captured image acquisition circuit configured to acquire a first captured image obtained by capturing light from an observation target to which light of a first wavelength band is emitted and a second captured image obtained by capturing fluorescence from the observation target excited by excitation light of a second wavelength band different from the first wavelength band;
an evaluation value calculation circuit configured to calculate, based on the first captured image, an evaluation value to be used for at least one of a first control of controlling a focus position of an image sensor configured to generate each of the first captured image and the second captured image and a second control of controlling a brightness of the first captured image and the second captured image;
an operation control circuit configured to execute at least one of the first control and the second control based on the evaluation value;
a light source control circuit configured to repeatedly execute light emission in which a first period of emitting light in the first wavelength band from a light source, a second period of emitting the excitation light from the light source, and a third period of emitting light in a third wavelength band different from the first wavelength band or the second wavelength band from the light source, are combined with each other in a specific time-division light emission pattern; and
an imaging control circuit configured to
control the image sensor to capture the light from the observation target to which the light in the first wavelength band is emitted in the first period so as to generate the first captured image,
control the image sensor to capture the fluorescence from the observation target excited by the excitation light in the second period so as to generate the second captured image, and
control the image sensor to capture the light from the observation target to which the light in the third wavelength band is emitted in the third period so as to generate a third captured image.

13. The medical image processing apparatus according to claim 12, wherein the second control includes a control of brightness of the first captured image, the second captured image, and the third captured image.

14. The medical image processing apparatus according to claim 12, wherein the specific time-division light emission pattern uses a combination of the periods so that the number of the first period is to be larger than the number of the second period and the number of the third period.

15. The medical image processing apparatus according to claim 14, wherein the specific time-division light emission pattern uses a combination of the periods in which the first period is arranged so as not to allow the second period and the third period to be adjacent to each other in time series.

16. The medical image processing apparatus according to claim 12, wherein the light in the third wavelength band is light in a near-infrared wavelength band that excites indocyanine green.

17. The medical image processing apparatus according to claim 12, wherein the light in the third wavelength band is light obtained by combining light in a green wavelength band and light in a blue wavelength band.

18. The medical image processing apparatus according to claim 12, wherein the third captured image is fluorescence image.

19. The medical image processing apparatus according to claim 12, further comprising:
a display control circuit configured to control a video signal to display the first captured image, the second captured image and the third captured image simultaneously on one or more monitor.

20. The medical image processing apparatus according to claim 19, wherein the display control circuit is configured to generate a display image based on the second and third image.

21. The medical image processing apparatus according to claim 20, wherein the display control circuit configured to generate a superimposed image where the second captured image and the third captured image are superimposed on the first captured image.

22. A medical observation system comprising:
a light source configured to emit light in a first wavelength band and excitation light in a second wavelength band different from the first wavelength band;
an image sensor configured to generate a first captured image by capturing light from an observation target to which light in the first wavelength band is emitted and that generates a second captured image by capturing fluorescence from the observation target excited by the excitation light; and
a medical image processing apparatus configured to process the first captured image and the second captured image,
wherein the medical image processing apparatus includes:
  a captured image acquisition circuit configured to acquire the first captured image and the second captured image;
  an evaluation value calculation circuit configured to calculate
    a focus evaluation value, based only on the first captured image, to be used for controlling a focus position of an image sensor configured to generate each of the first captured image and the second captured image, and
    a brightness evaluation value relating to at least one of an exposure time, a gain for image generation, a gain for image processing and an amount of light output by the light source, based on the first captured image, to be used for controlling a brightness of the first captured image and a brightness of the second captured image; and
an operation control circuit configured to
  control the focus position of the image sensor based on the focus evaluation value to generate both the first captured image and the second captured image,
  adjust the brightness of the first captured image based on the brightness evaluation value, and
  adjust the brightness of the second captured image based on a correlation between the first captured image and the second captured image, and the brightness evaluation value.

23. The medical observation system according to claim 22, further comprising:
a light source control circuit configured to repeatedly execute light emission in which a first period of emitting light in the first wavelength band from a light source, a second period of emitting the excitation light from the light source, and a third period of emitting light in a third wavelength band different from the first wavelength band or the second wavelength band from the light source, are combined with each other in a specific time-division light emission pattern; and
an imaging control circuit configured to
  control the image sensor to capture the light from the observation target to which the light in the first wavelength band is emitted in the first period so as to generate the first captured image,
  control the image sensor to capture the fluorescence from the observation target excited by the excitation light in the second period so as to generate the second captured image, and
  control the image sensor to capture the light from the observation target to which the light in the third wavelength band is emitted in the third period so as to generate a third captured image.

24. The medical observation system according to claim 23, wherein the second control includes a control of brightness of the first captured image, the second captured image, and the third captured image.

25. The medical observation system according to claim 23, wherein the specific time-division light emission pattern uses a combination of the periods so that the number of the first period is to be larger than the number of the second period and the number of the third period.

26. The medical image processing apparatus according to claim 25, wherein the specific time-division light emission pattern uses a combination of the periods in which the first period is arranged so as not to allow the second period and the third period to be adjacent to each other in time series.

27. The medical observation system according to claim 23, wherein the light in the third wavelength band is light in a near-infrared wavelength band that excites indocyanine green.

28. The medical observation system according to claim 23, wherein the light in the third wavelength band is light obtained by combining light in a green wavelength band and light in a blue wavelength band.

\* \* \* \* \*